(12) United States Patent
Lim et al.

(10) Patent No.: US 8,575,173 B2
(45) Date of Patent: Nov. 5, 2013

(54) PIPERAZINYL 3-AMINOPYRROLIDINE DERIVATIVES AS A CCR2 ANTAGONISTS

(75) Inventors: Jee Woong Lim, Gyeonggi-do (KR); Jong-Hoon Kim, Gyeonggi-do (KR); Min-Ho Oak, Gyeonggi-do (KR); Yongho Na, Gyeonggi-do (KR); Youna Oh, Seoul (KR); So-Hee Kang, Daejeon (KR); Jung-Ok Lee, Gyeonggi-do (KR); Jung-Duk Sohn, Gyeonggi-do (KR); Seung-Woo Lee, Seoul (KR)

(73) Assignee: Yang Ji Chemical Co., Ltd. (KR)

( * ) Notice: Subject to any disclaimer, the term of this patent is extended or adjusted under 35 U.S.C. 154(b) by 19 days.

(21) Appl. No.: 13/383,104

(22) PCT Filed: Jun. 11, 2010

(86) PCT No.: PCT/KR2010/003790
§ 371 (c)(1),
(2), (4) Date: Jan. 9, 2012

(87) PCT Pub. No.: WO2011/004972
PCT Pub. Date: Jan. 13, 2011

(65) Prior Publication Data
US 2012/0190689 A1    Jul. 26, 2012

(30) Foreign Application Priority Data

Jul. 10, 2009   (KR) .................... 10-2009-0063136

(51) Int. Cl.
*A61K 31/496*    (2006.01)
*C07D 403/06*    (2006.01)

(52) U.S. Cl.
USPC ..................... 514/254.01; 544/372

(58) Field of Classification Search
USPC ..................... 514/254.01; 544/372
See application file for complete search history.

(56) References Cited

FOREIGN PATENT DOCUMENTS

| EA | 010027 | 6/2008 |
|---|---|---|
| EP | 1553085 | 7/2005 |
| WO | 00/69432 | 11/2000 |
| WO | 03/075853 | 9/2003 |
| WO | 2004/050024 | 6/2004 |
| WO | 2006/036527 | 4/2006 |
| WO | 2007/053495 | 5/2007 |
| WO | 2007/053498 | 5/2007 |
| WO | 2007/053499 | 5/2007 |
| WO | 2007/106797 | 9/2007 |

OTHER PUBLICATIONS

Lim et al., Synthesis and biological evaluation of 3-aminopyrrolidine derivatives as CC chemokine receptor 2 antagonists, 2010, Bioorganic & Medicinal Chemistry Letters, 20, 2099-2102.*
Vippagunta et al., Crystalline solids, 2001, Advanced Drug Delivery Reviews, 48, pp. 3 and 18.*
Matthias K. Schwarz, et al., "New Therapeutics that Modulate Chemokine Networks," Nature Reviews, May 2002, pp. 347-358, vol. 1, Nature Publishing Group.
Joseph El Khoury, et al., "Ccr2 Deficiency Impairs Microglial Accumulation and Accelerates Progression of Alzheimer-like Disease," Nature Medicine, Apr. 2007, pp. 432-438, vol. 13, No. 4.
Justin I. Odegaard, et al., "Macrophage-specific PPAR Controls Alternative Activation and Improves Insulin Resistance," Nature, Jun. 28, 2007, pp. 1116-1121, vol. 447, Nature Publishing Group.
Landin Boring, et al., "MCP-1 in Human Disease," Chemokines in Disease: Biology and Clinical Research, pp. 53-65, Humana Press Inc., Totowa, NJ, 1999.
Jeffrey H. Ruth, et al., "Selective Lymphocyte Chemokine Receptor Expression in the Rheumatoid Joint," Arthritis & Rheumatism, Dec. 2001, pp. 2750-2760, vol. 44, No. 12, Wiley-Liss, Inc.
Korean Office Action—Korean Application No. 10-2009-0063136 issued on Apr. 29, 2011, citing WO 2003-075853 and WO 2007-053498.
International Search Report—PCT/KR2010/003790 dated Mar. 31, 2011.
Russian Office Action—Russian Application No. 2012104633 issued on Dec. 24, 2012, citing EA010027, WO2007053498, and EP1553085.
W. J. Moree, et al., Potent antagonists of the CCR2b receptor. Part 3:SAR of the (R)-3-aminopyrrolidine series, Bioorganic & Medical Chemistry Letters, 2008, pp. 1869-1873.
J. W. Lim, et al., Synthesis and biological evaluation of 3-aminopyrrolidine derivatives as CC chemokine receptor 2 antagonists, Bioorganic & Medicinal Chemistry Letters 20, 2010, pp. 2009-2102.
European Search Report—European Application No. 10797246.5 issued on Nov. 26, 2012, WO2007/053498, Moree, et al., "Potent antagonists of the CCR2b receptor. Part 3:SAR of the (R)-3-aminopyrrolidine series" and Lim, et al., "Synthesis and biological evaluation of 3-aminopyrrolidine derivatives as CC chemokine receptor 2 antagonists".

* cited by examiner

*Primary Examiner* — Kristin Vajda
(74) *Attorney, Agent, or Firm* — Cantor Colburn LLP

(57) ABSTRACT

The present invention relates to compounds of chemical formula 1 and having CCR2 (chemokine receptor 2) antagonistic effects, and salts or isomers thereof. These compounds are very useful for treating, preventing, or relieving rheumatoid arthritis, arteriosclerosis, multiple sclerosis, asthma, and various diseases related to CCR2.

[Formula 1]

wherein $R_1$, $R_2$, $R_3$, $R_4$, $R_5$, $R_6$, $R_7$, $R_8$ and $R_9$ is the same as defined in the specification.

6 Claims, No Drawings

PIPERAZINYL 3-AMINOPYRROLIDINE DERIVATIVES AS A CCR2 ANTAGONISTS

FIELD OF THE INVENTION

The present invention relates to novel, useful compounds with antagonistic effect against chemokine receptor 2 (CCR2) in human body as therapeutic agents for inflammation and other various disease. Specifically the invention relates to provide new useful compounds to treat or improve such physiologically related diseases for example, rheumatoid arthritis, arteriosclerosis, multiple sclerosis, asthma and CCR2 related several diseases, testing effect of the activity of the derivatives of 3-aminopyrrolidine which show antagonistic action against CCR2, monocyte chemotactic protein-1 (receptor of MCP-1).

BACKGROUND ART

The chemokines had been characterized into about 50 types up to now as physiologically active proteins acting on immune system in human body and are classified into 4 groups including C, CC, CXC and CX3C based on the structural difference of conserved cystein sharing in amino acid sequence. Each chemokines bind to GPCR (G-protein-coupled receptor) and show their physiological action, where especially receptor with which MCP-1, CC chemokine, integrates is said to be CCR2. MCP-1 is known to play a major role in migration of monocytes during process leading to inflammation (reference: Nature Review Drug Discovery, 2002, 1, 347). For example, in rheumatoid arthritis overexpression of MCP-1 and CCR2 were identified (reference: Arthritis Rheum., 2001, 44, 2750) and the role of MCP-1 and CCR2 were also demonstrated by extensive research in knockout mouse (reference: Chemokine in Disease, 1999, 53-65).

Since CCR2 is considered to be a target of prominent drug of inflammatory diseases, several therapeutic agents for the inflammatory related several diseases could be developed based on the CCR2 antagonistic effect. For example, Johnson & Johnson tried to develop dipiperidine compounds as CCR2 antagonists. These compounds showed high affinity to CCR2 receptor and also blocked chemotaxis induced by MCP-1 in THP-1 cell lines (reference: WO2006-036527, WO2007-106797).

The Millenium also developed human monoclonal antibody MLN1202 as its therapeutic agent for inflammatory disease so that it demonstrated CCR2 to be a target of prominent drug of inflammatory disease, getting positive results from clinical trial aiming at arteriosclerosis.

Meanwhile obesity and insulin resistance, which is important characteristic of metabolic syndrome, is closely correlated with inflammation. If chronic overnutrition is lasting, macrophage in adipose tissue is infiltrated and thus the local inflammation is brought out, which intensifies the resistance to insulin. At this time inhibiting MCP-1 or its own receptor CCR2 suppresses migration of macrophage into adipose tissue, which may decrease inflammation in the adipose tissue and increase sensitivity to insulin. Based on the animal test result, it may be observed that the intake of CCR2 deficient mouse was decreased than normal one, but obesity was not developed obviously even with high fat diet (reference: Nature, 2007, 447, 1116).

The CCR2 could also be useful as therapeutic agent for Alzheimer's disease. The accumulative process of amyloid-beta, which is protein as form of plaque and is produced in the brain of Alzheimer's disease patients, is known to be associated with pathways of inflammatory response regulated by microglias, immune cells of brain and central nervous system. The CCR2 has a major role in migration of this microglia (reference: Nature Medicine, 2007, 13, 432).

It is prior art to have 3-aminopyrrolidine as core structure among low molecular weight compound representing antagonistic effect of CCR2 receptor. And it was proposed according to WO 2004-050024, for example, a representative structure where cycloalkane was integrated into 3-aminopyrrolidine. According to WO 2000-069432, the compound where alkyl and again aryl or cycloalkyl group were integrated into 3-aminopyrrolidine was suggested. The representative structure of such compounds were 3-amino-N-benzylpyrrolidine of which antagonistic action to CCR2 receptor had been already reported.

As suggested by WO 2003-075853, the compound was notified where arylsulfone group was substituted on the carbon atom of 3-aminopyrrolidine as more diverse structure compound including 3-aminopyrrolidine structure. Meanwhile, according to WO 2007-053495, WO 2007-053498, WO 2007-053499, cycloalkanes including heteroatoms which are connected to 3-aminopyrrolidine were also proposed.

DETAILED DESCRIPTION OF THE INVENTION

Technical Problem

It is an object of the present invention to provide compounds having the formula I, its pharmaceutically acceptable salts, enantiomers, hydrates, solvates and crystalline polymorphs which strongly inhibit the interaction between MCP-1 and CCR2 as novel compounds containing piperazinylethyl 3-aminopyrrolidine structure.

A further object of the invention is to provide pharmaceutical compositions containing, as an active ingredient, compounds with the formula I or its pharmaceutically acceptable salts for prevention, treatment or improvement of the CCR2 mediated inflammatory diseases and symptoms.

Another object of the invention is to provide use of compounds having the formula I or pharmaceutically acceptable salts thereof as vasoprotective agents or immunosuppressants.

Technical Solution

Compounds of the present invention to accomplish their objects as described are characterized by the following structure of the formula I:

[Formula I]

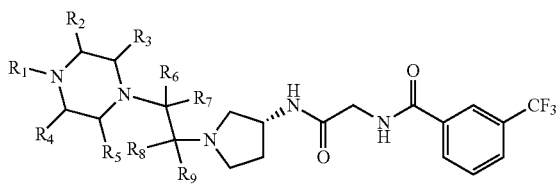

[Formula 2]

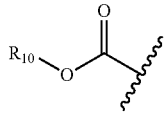

[Formula 3]

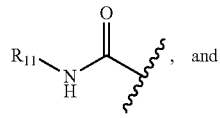
, and

[Formula 4]

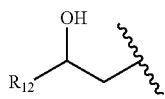

wherein: $R_1$ could be independently selected from groups consisting of hydrogen atom, $C_1$-$C_3$ alkyl, phenyl, benzyl, benzoyl, benzensulfonyl, $C_1$-$C_3$ alkylcarbonyl, $C_3$-$C_7$ cycloalkyl, the formula II, III and IV;

$R_{10}$, $R_{11}$ and $R_{12}$ could be independently selected from groups consisting of hydrogen atom, $C_1$-$C_3$ alkyl, phenyl, and benzyl;

all benzene groups included as part of $R_1$ could have the substituent independently selected from groups consisting of $C_1$-$C_3$ alkyl, $C_1$-$C_2$ haloalkyl, halogen atom and cyano;

$R_2$, $R_3$, $R_4$, $R_5$, $R_6$, $R_7$, $R_8$ and $R_9$ could be independently selected from hydrogen atom and $C_1$-$C_3$ alkyl;

$R_6$ and $R_7$, $R_8$ and $R_9$ could be independently selected as carbonyl group;

wherein said halogen is selected from groups consisting of fluorine, chlorine and bromine atom.

And, the compound of the invention having the formula I may be selected from groups consisting of N-{[1-(2-(1-(phenylaminocarbonyl)-piperazine-4-yl)ethyl)-pyrrolidine-(3R)-yl-carbamoyl]-methyl}-3-trifluoromethylbenzamide, N-{[1-(2-(1-(p-tolylaminocarbonyl)-piperazine-4-yl)-ethyl)-pyrrolidine-(3R)-yl-carbamoyl]-methyl}-3-trifluoromethylbenzamide, N-{[1-(2-(1-(4-chlorophenylaminocarbonyl)-piperazine-4-yl)-ethyl)-pyrrolidine-(3R)-yl-carbamoyl]-methyl}-3-trifluoromethylbenzamide, N-{[1-(2-(1-(methoxycarbonyl)-piperazine-4-yl)ethyl)-pyrrolidine-(3R)-yl-carbamoyl]-methyl}-3-trifluoromethylbenzamide, N-{[1-(2-(1-(ethoxycarbonyl)-piperazine-4-yl)ethyl)-pyrrolidine-(3R)-yl-carbamoyl]-methyl}-3-trifluoromethylbenzamide, N-{[1-(2-(4-benzoylpiperazine-1-yl)ethyl)-pyrrolidine-(3R)-yl-carbamoyl]-methyl}-3-trifluoromethylbenzamide, N-{[1-(2-(4-(2-methylbenzoyl)piperazine-1-yl)ethyl)-pyrrolidine-(3R)-yl-carbamoyl]-methyl}-3-trifluoromethylbenzamide, N-{[1-(2-(4-(3-methylbenzoyl)piperazine-1-yl)ethyl)-pyrrolidine-(3R)-yl-carbamoyl]-methyl}-3-trifluoromethylbenzamide, N-{[1-(2-(4-(4-methylbenzoyl)piperazine-1-yl)ethyl)-pyrrolidine-(3R)-yl-carbamoyl]-methyl}-3-trifluoromethylbenzamide, N-{[1-(2-(4-(4-fluorobenzoyl)piperazine-1-yl)ethyl)-pyrrolidine-(3R)-yl-carbamoyl]-methyl}-3-trifluoromethylbenzamide, N-{[1-(2-(4-(4-cyanobenzoyl)piperazine-1-yl)ethyl)-pyrrolidine-(3R)-yl-carbamoyl]-methyl}-3-trifluoromethylbenzamide, N-{[1-(2-(4-(4-ethylbenzoyl)piperazine-1-yl)ethyl)-pyrrolidine-(3R)-yl-carbamoyl]-methyl}-3-trifluoromethylbenzamide, N-{[1-(2-(4-(phenylsulfonyl)piperazine-1-yl)ethyl)-pyrrolidine-(3R)-yl-carbamoyl]-methyl}-3-trifluoromethylbenzamide, N-{[1-(2-(4-propionylpiperazine-1-yl)ethyl)-pyrrolidine-(3R)-yl-carbamoyl]-methyl}-3-trifluoromethylbenzamide, N-{[1-(2-(4-benzylpiperazine-1-yl)ethyl)-pyrrolidine-(3R)-yl-carbamoyl]-methyl}-3-trifluoromethylbenzamide, N-{[1-(1-(4-benzoylpiperazine-1-yl)propane-2-yl)-pyrrolidine-(3R)-yl-carbamoyl]-methyl}-3-trifluoromethylbenzamide, N-{[1-(3-(4-benzoylpiperazine-1-yl)butane-2-yl)-pyrrolidine-(3R)-yl-carbamoyl]-methyl}-3-trifluoromethylbenzamide, N-{[1-(2-(4-benzoylpiperazine-1-yl)propane-1-yl)-pyrrolidine-(3R)-yl-carbamoyl]-methyl}-3-trifluoromethylbenzamide, N-{[1-(1-(4-benzoylpiperazine-1-yl)butane-2-yl)-pyrrolidine-(3R)-yl-carbamoyl]-methyl}-3-trifluoromethylbenzamide, N-{[1-(2-(4-benzoylpiperazine-1-yl)butyl)-pyrrolidine-(3R)-yl-carbamoyl]-methyl}-3-trifluoromethylbenzamide, N-{[1-(2-(4-benzoylpiperazine-1-yl)-2-methylpropyl)-pyrrolidine-(3R)-yl-carbamoyl]-methyl}-3-trifluoromethylbenzamide, N-{[1-(1-(4-benzoylpiperazine-1-yl)-2-methylpropan-2-yl)-pyrrolidine-(3R)-yl-carbamoyl]-methyl}-3-trifluoromethylbenzamide, N-{[1-(3-(4-(3-chlorophenyl)piperazine-1-yl)butane-2-yl)-pyrrolidine-(3R)-yl-carbamoyl]-methyl}-3-trifluoromethylbenzamide, N-{[1-(1-(4-phenylpiperazine-1-yl)propan-2-yl)-pyrrolidine-(3R)-yl-carbamoyl]-methyl}-3-trifluoromethylbenzamide, N-{[1-(1-(4-cyclohexylpiperazine-1-yl)propan-2-yl)-pyrrolidine(3R)-yl-carbamoyl]-methyl}-3-trifluoromethylbenzamide, N-{[1-(2-(4-(2-hydroxybutyl)piperazine-1-yl)ethyl)-pyrrolidine-(3R)-yl-carbamoyl]-methyl}-3-trifluoromethylbenzamide, N-{[1-(2-(4-(2-hydroxy-2-methylpropyl)piperazine-1-yl)ethyl pyrrolidine-(3R)-yl-carbamoyl]-methyl}-3-trifluoromethylbenzamide, N-{[1-(2-(4-(2-hydroxy-2-phenylethyl)piperazine-1-yl)ethyl)-pyrrolidine-(3R)-yl-carbamoyl]-methyl}-3-trifluoromethylbenzamide, N-{[1-(2-(4-(2-(4-chlorophenyl)-2-hydroxyethyl)piperazine-1-yl)ethyl)-pyrrolidine-(3R)-yl-carbamoyl]-methyl}-3-trifluoromethylbenzamide, N-{[1-(2-(4-benzoylpiperazine-1-yl)-2-oxoethyl)-pyrrolidine-(3R)-yl-carbamoyl]-methyl}-3-trifluoromethylbenzamide, N-{[1-(2-(4-(4-methylbenzoyl)piperazine-1-yl)-2-oxoethyl)-pyrrolidine-(3R)-yl-carbamoyl]-methyl}-3-trifluoromethylbenzamide, N-{[1-(2-(4-(4-ethylbenzoyl)piperazine-1-yl)-2-oxoethyl)-pyrrolidine-(3R)-yl-carbamoyl]-methyl}-3-trifluoromethylbenzamide, N-{[1-(2-(4-(3-methylbenzoyl)piperazine-1-yl)-2-oxoethyl)-pyrrolidine-(3R)-yl-carbamoyl]-methyl}-3-trifluoromethylbenzamide, N-{[1-(2-(4-(2-methylbenzoyl)piperazine-1-yl)-2-oxoethyl)-pyrrolidine-(3R)-yl-carbamoyl]-methyl}-3-trifluoromethylbenzamide, N-{[1-(2-(4-phenylpiperazine-1-yl)-2-oxoethyl)-pyrrolidine-(3R)-yl-carbamoyl]-methyl}-3-trifluoromethylbenzamide, N-{[1-(2-(4-(benzoxycarbonyl)piperazine-1-yl)-2-oxoethyl)-pyrrolidine-(3R)-yl-carbamoyl]-methyl}-3-trifluoromethylbenzamide, and N-{[1-(2-(4-benzoyl-2,5-dimethylpiperazine-1-yl)ethyl)-pyrrolidine-(3R)-yl-carbamoyl]-methyl}-3-trifluoromethylbenzamide.

The present invention further relates to the pharmaceutically acceptable salts, enantiomers or stereoisomers, hydrates, solvates or crystalline polymorphs forms of said compound having the formula I.

Meanwhile, the present invention is characterized by pharmaceutical compositions containing as an active ingredient, compounds having the formula I or pharmaceutically acceptable salts for prevention, treatment or improvement of CCR2 mediated inflammatory diseases and symptoms.

The characteristics of said pharmaceutical compositions should be also vasoprotective agents or immunosuppressants.

The said CCR2 mediated inflammatory diseases and symptoms may be selected from groups consisting of allergic rhinitis, respiratory allergic disease, chronic obstructive pulmonary, asthma, pneumonia, rhematic arthritis, uveitis, multiple sclerosis, contact dermatitis, atopic dermatitis, Crohn's disease, colitis, nephritis, diabetes mellitus, diabetic complication, obesity, hyperlipidemia, arteriosclerosis and restenosis.

Meanwhile, the present invention is characterized by use of compounds having the formula I or pharmaceutically acceptable salts thereof as vasoprotective agents or immunosuppressants.

Advantageous Effect

The compounds of the present invention having the formula I were shown to have high affinity to said CCR2 receptor protein and efficiently suppress $Ca^{2+}$ flux and chemotaxis even within the range of low concentration.

And it was found that the inhibitory level to CYP450 was relatively low and the compounds were safe with little cardiotoxicity and cytotoxicity.

Accordingly, the compound of the present invention may be useful to treat, prevent or improve rheumatic arthritis, arteriosclerosis, multiple sclerosis, asthma and other various diseases associated with CCR2.

[Working Mode]

Hereinafter, preferred embodiments of the present invention will be described in detail. In the following descriptions, many definitions and specifications such as specific constituent elements will be described. However, it will be obvious to those having ordinary skill in the art that these definitions and specifications are provided only for illustrative purposes and are not intended to limit the present invention by any means. Further, in the following descriptions, if it is considered that any specific description on a related known function or constitution may make the gist of the present invention unnecessarily ambiguous, detailed descriptions on the function or constitution will not be given in the present specification.

The present invention provides compounds having the formula I or its isomer and pharmaceutically acceptable salts thereof which show CCR2 antagonism.

[Formula I]

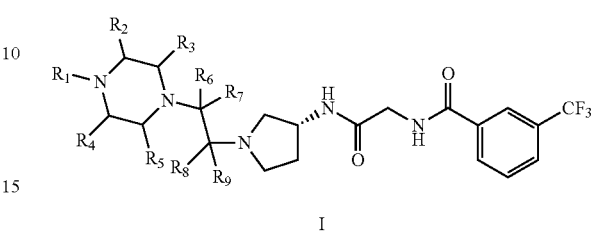

[Formula 2]

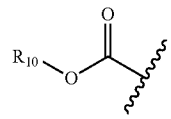

[Formula 3]

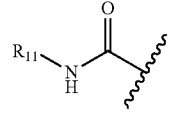

[Formula 4]

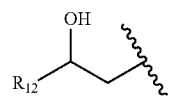

wherein $R_1$ could be independently selected from groups consisting of hydrogen atom, $C_1$-$C_3$ alkyl, phenyl, benzyl, benzoyl, benzensulfonyl, $C_1$-$C_3$ alkylcarbonyl, $C_3$-$C_7$ cycloalkyl, the formula II, III and IV;

$R_{10}$, $R_{11}$ and $R_{12}$ could be independently selected from groups consisting of hydrogen atom, $C_1$-$C_3$ alkyl, phenyl, and benzyl;

all benzene groups included as part of $R_1$ could have the substituent independently selected from groups consisting of $C_1$-$C_3$ alkyl, $C_1$-$C_2$ haloalkyl, halogen atom and cyano;

$R_2$, $R_3$, $R_4$, $R_5$, $R_6$, $R_7$, $R_8$ and $R_9$ could be independently selected from hydrogen atom and $C_1$-$C_3$ alkyl;

$R_6$ and $R_7$, $R_8$ and $R_9$ could be independently selected as carbonyl group;

wherein said halogen is selected from groups consisting of fluorine, chlorine and bromine atom.

The present invention relates to compounds of formula I and its pharmaceutically acceptable salts, geometrical isomer or enantiomer, hydrates, solvates or crystalline polymorphs which act via antagonism to interaction between MCP-1 and CCR2 receptor and thus have treating effect to the several diseases associated with CCR2 via anti-inflammatory and immunoregulatory action.

The term 'pharmaceutically acceptable salts' means acid addition salts or base addition salts of the compounds provided by the present invention. These salts may be prepared by the conventional organic synthetic method, depending on specific functionalities on the compounds described herein. Herein addition acids or bases are non-toxic or relatively low toxic so that they may be used to prepare such drugs. When the compounds of the present invention are basic, a proper amount of acids should be added to form salts. Herein the desirable acid for addition salts include inorganic acid such as hydrochloric acid, bromic acid, nitric acid, sulfuric acid, iodic acid and organic acid such as acetic acid, citric acid, fumaric acid, galactamic acid, malonic acid, maleic acid, succinic acid, tartaric acid, methanesulfonic acid, lactic acid, oxalic acid, propionic acid, salicylic acid, mandelic acid, phthalic acid, etc. When the compounds of the invention is acidic, an appropriate amount of bases should be added to form salts. Herein the desirable base for addition of the desired salts include ammonium, sodium, potassium, calcium, magnesium, organic ammonium, etc.

Meanwhile, the compounds proposed herein include compounds not solvated or hydrates containing water or solvates containing organic solvent used in the conventional process of organic synthesis, and all those anhydrides, hydrates, solvates are intended to be encompassed within the scope of the present invention.

Meanwhile the compounds proposed herein as solid may exist in amorphous forms or multiple crystalline polymorphs and those amorphous or each crystalline polymorphs are intended to be encompassed within the scope of the present invention.

The compounds of the present invention can be prepared by conventional organic synthesis technology in a number of ways. The 3-aminopyrrolidine structure commonly contained in the compounds of the present invention may be introduced in a number of ways based on commercially available raw materials. Specifically, the compounds of the present invention may be synthesized, depending on the methods suggested from reaction formula I to VI below.

According to the following reaction formula I, the preparatory method of the common intermediates could be provided to prepare the compounds of the present invention. The raw material used to introduce the structure of 3-aminopyrrolidine is (3R)-(−)-1-benzyl-3-aminopyrrolidine like the compound (3). Herein the C-3 position of pyrrolidine ring exist as chiral form, and all compounds suggested herein including 3-aminopyrrolidine structure are limited to (R)-form based on the nomenclature of compound (3).

[Reaction Formula I]

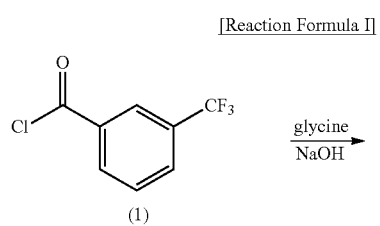

(1)

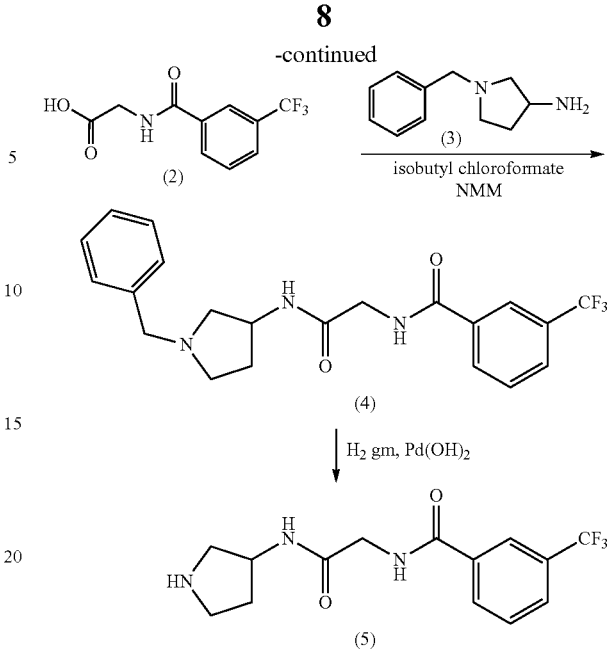

According to said reaction formula I, the compound (2) can be synthesized by reacting compound (1) as commercially available starting material with glycine, a type of amino acid, under alkaline and aqueous condition. It may be accomplished according to a number of notified methods how compound (3), the chiral 3-aminopyrrolidine derivative described above, may react with compound (2) to form amide bond. In the present specification, isobutyl chloroformate is illustrated as a way to activate carboxylic acid of compound (2), herein Compound (4) can be easily prepared by using NMM (N-methylmorpholine) as base. Since N-benzyl group of compound (4) acts as protective agent, benzyl groups should be deprotected to convert pyrrolidine structure with N-alkylated and other N-substituents. As a conventional way to such reaction, compound (5) can be easily prepared using hydrogen atom under Pd(OH)$_2$ catalyst. Thus prepared compound (5) may be used as key intermediate to prepare the compounds with various structure representing CCR2 antagonistic effect described herein.

Meanwhile, all those intermediate compounds prepared according to described method in the reaction formula I can be yielded in the solid state. Specifically the present invention provides easy preparatory method for industrial large production, which is meant to solidify target compound under non-polar solvent.

The synthesis of compounds (9) as CCR2 antagonist suggested in the present invention can be proceeded according to formula II below.

[Reaction Formula 2]

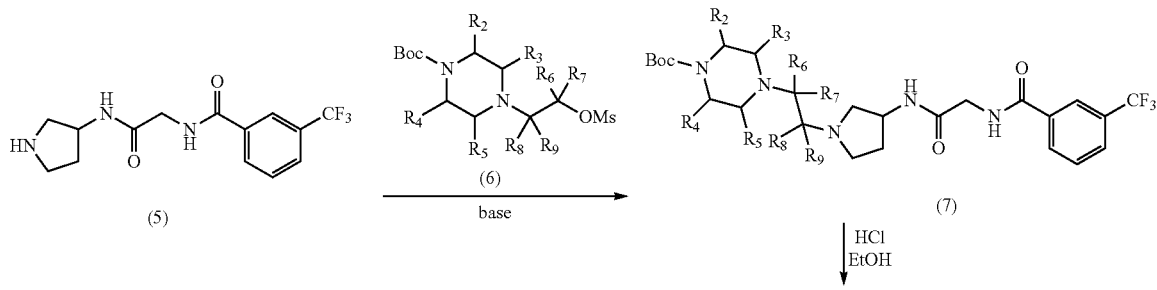

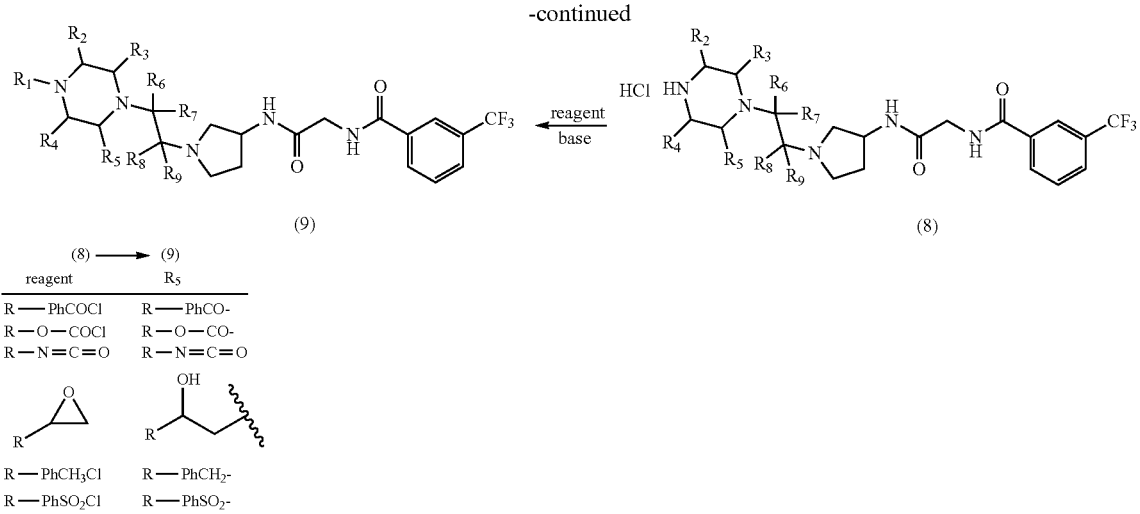

| (8) → (9) | |
|---|---|
| reagent | R$_5$ |
| R—PhCOCl | R—PhCO- |
| R—O—COCl | R—O—CO- |
| R—N=C=O | R—N=C=O |
| epoxide R | R—CH(OH)CH$_2$- |
| R—PhCH$_3$Cl | R—PhCH$_2$- |
| R—PhSO$_2$Cl | R—PhSO$_2$- |

The intermediate compounds (7) were yielded by reacting compound (5) prepared according to method in reaction formula I above as starting material with piperazinylethanemesylate (6) protected with t-butoxycarbonly group and substituted at R$_2$, R$_3$, R$_4$, R$_5$, R$_6$, R$_7$, R$_8$ and R$_9$ under alkaline condition. Herein R$_2$, R$_3$, R$_4$, R$_5$, R$_6$, R$_7$, R$_8$ and R$_9$ are same as defined at present specification.

The piperazine intermediates (8) in hydrochloride form are yielded by deprotecting intermediates (7) with ethanol saturated with hydrochloric acid. The compound (9) as CCR2 antagonist desired in the present invention can be prepared by reacting these compounds with the various reagents under alkaline condition.

R$_8$ and R$_9$ or chloroethanol derivatives under alkaline condition, wherein R$_6$, R$_7$, R$_8$ and R$_9$ are same as defined in specification.

Intermediate compound (11) can be yielded by reacting ethanol derivatives (10) with methanesulfonyl chloride (MsCl) under alkaline condition, but the compound (11) could be proceeded to the next reaction with purification, separation process or without purification process if required. Intermediate (11) is reacted with piperazine derivative (12) substituted by R$_1$, R$_2$, R$_3$, R$_4$ and R$_5$ under alkaline condition to prepare the compound (9) desired in the present invention. Herein piperazine derivative (12) used can take hydrochloride

[Reaction Formula 3]

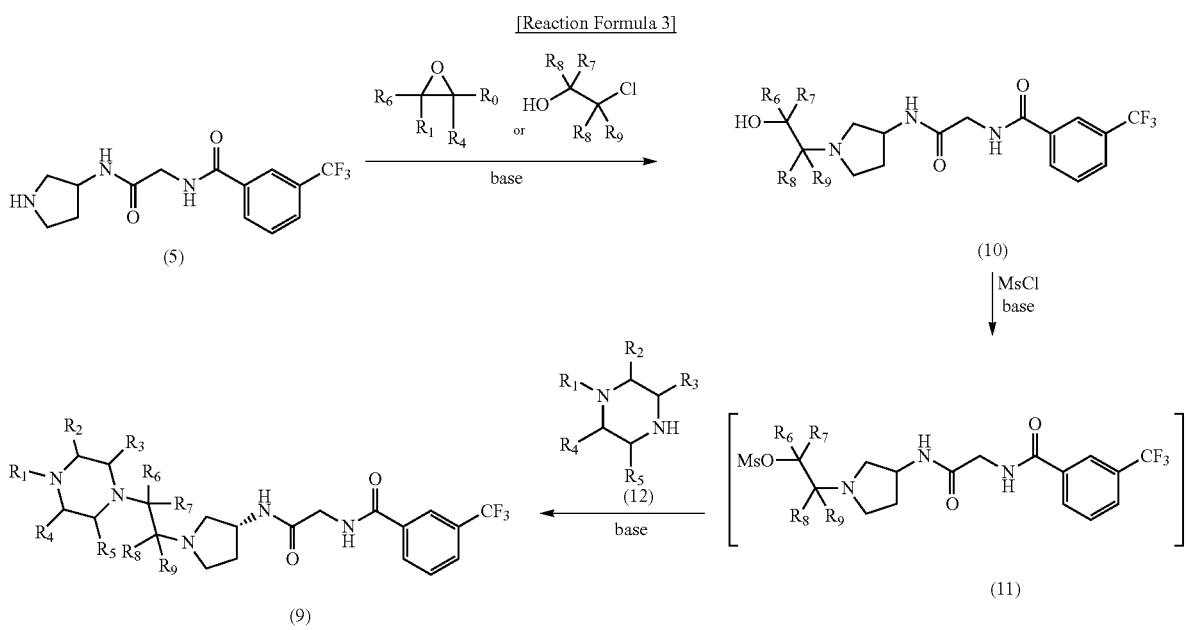

The reaction formula III could be used to prepare the compound (9) as CCR2 antagonist described in the present invention. The intermediate compound (10) is prepared by reacting compound (5) prepared according to the formula I above as starting material with epoxy compound substituted by R$_6$, R$_7$, form if required, wherein R$_1$, R$_2$, R$_3$, R$_4$ and R$_5$ are same as defined in the present specification.

Another method to prepare compound (9) as CCR2 antagonist described in the present invention is same as described on the reaction formula IV below.

[Reaction Formula 4]

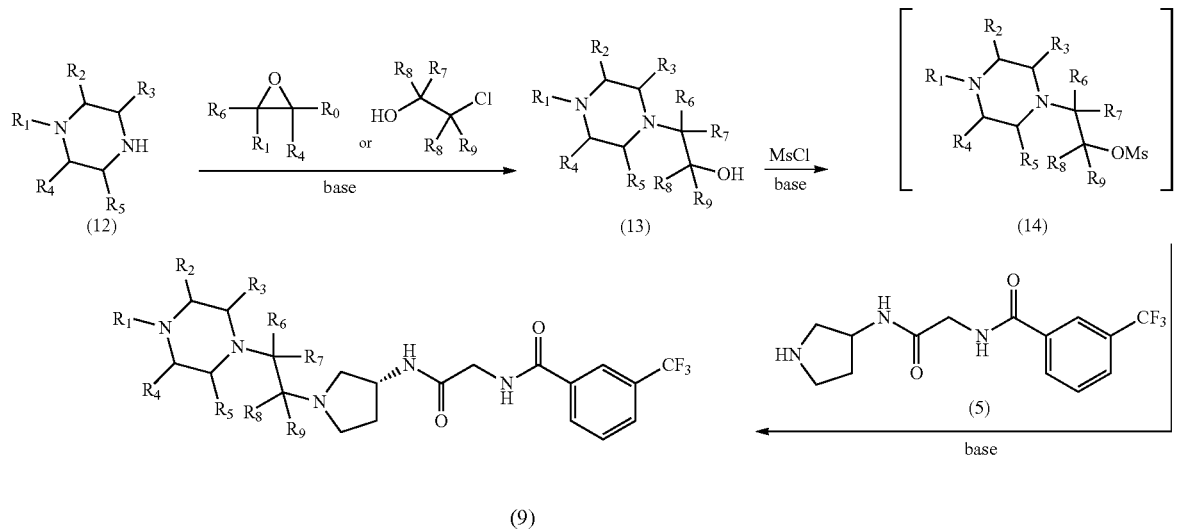

(9)

Intermediate compound (13) is prepared by reacting piperazine derivative (12) as starting material with epoxy compound or chloroethanol derivative substituted by $R_6$, $R_7$, $R_8$ and $R_9$ under alkaline condition. Herein $R_1$, $R_2$, $R_3$, $R_4$, $R_5$, $R_6$, $R_7$, $R_8$ and $R_9$ are same as defined on the present specification. Intermediate compound (14) can be yielded by reacting ethanol derivative (13) with mesyl chloride under alkaline condition, but compound (14) could be proceeded to the next reaction with purification, separation or without purification process if required. Compound (9) desired in the present invention can be prepared by reacting the intermediate (14) with pyrrolidine intermediate (5) under alkaline condition.

Another method to prepare compound (9) as CCR2 antagonist described on the present invention is same as defined on the reaction formula V below.

Intermediate compound (15) is prepared by reacting piperazine derivative (12) as starting material with 2-chloroketone derivative substituted by $R_6$, $R_7$ and $R_8$ under alkaline condition. Herein $R_1$, $R_2$, $R_3$, $R_4$, $R_5$, $R_6$, $R_7$ and $R_8$ are same as defined on the present specification. Target compound (9) can be prepared by reductive amination of pyrrolidine intermediate (5) with the intermediate compound (15). Herein reductants used may be selected among various methods notified, but easy method to prepare N-alkylpyrrolidine compound is illustrated by using sodium triacetoxyborohydride $(NaBH(OAc)_3)$ as a relatively low reductive reductant in the present specification.

Meanwhile $R_6$, $R_7$, $R_8$ and $R_9$ of the formula I defined on the present specification include carbonyl group and those compound (20) as CCR2 antagonists can be prepared according to the illustrated way on the reaction formula VI below.

[Reaction Formula 5]

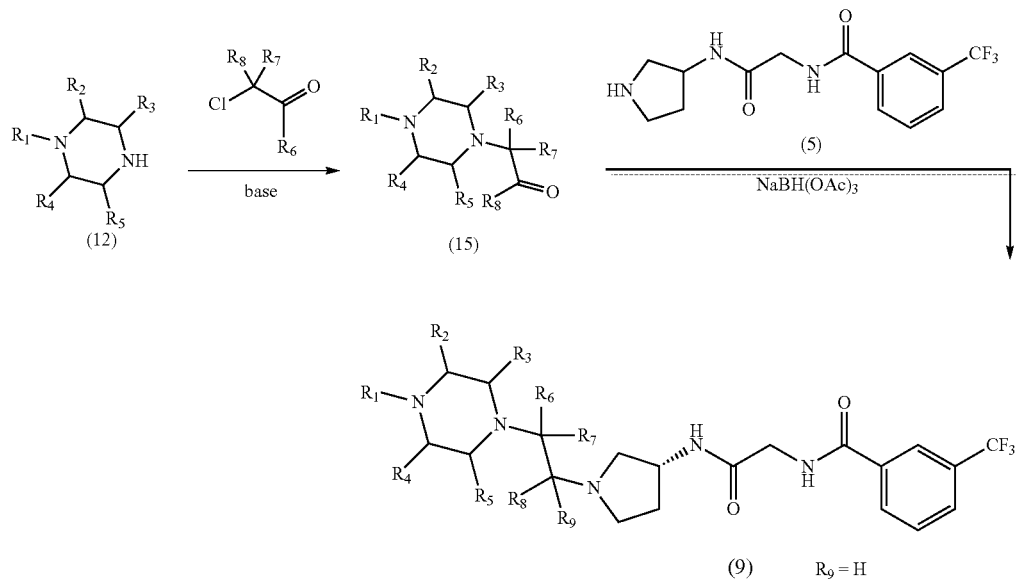

(9)  $R_9 = H$

[Reaction Formula 6]

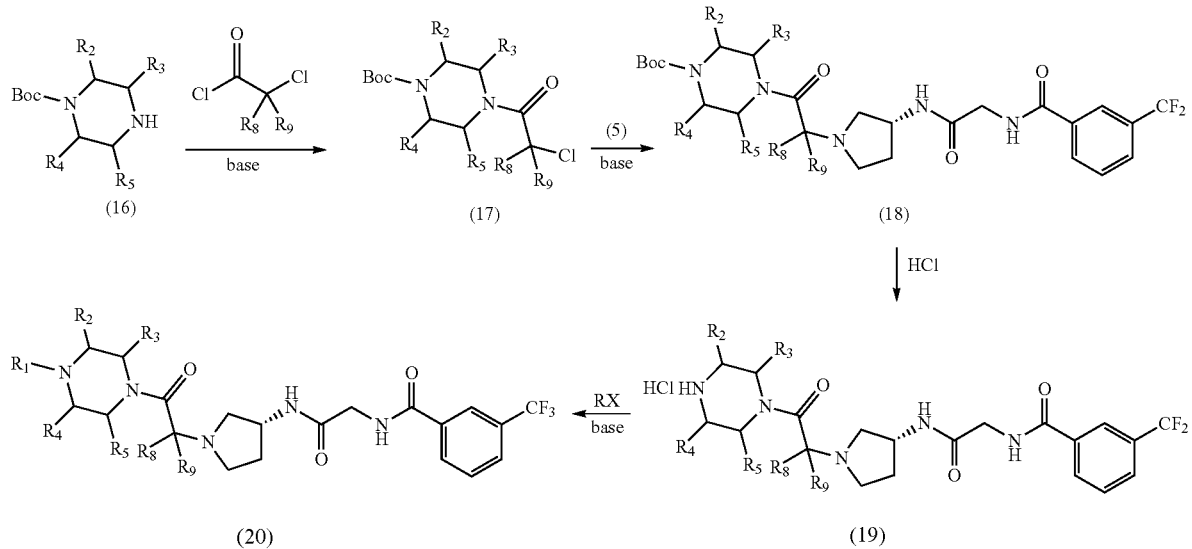

According to described procedure above, compound (17) may be prepared by reacting piperazine protected with t-butoxycarbonyl group (Boc) and substituted by $R_2$, $R_3$, $R_4$ and $R_5$ as a starting material with 2-chloroacetylchloride derivative substituted by $R_8$ and $R_9$ under alkaline condition. Herein $R_2$, $R_3$, $R_4$, $R_5$, $R_8$ and $R_9$ are same as defined on the present specification. Compound (18) may be prepared by substituting compound (17) with intermediate (5) under alkaline condition and then removing the protecting group under acidic condition in suitable solvent leads to yield compound (19). Compound (20) as CCR2 antagonist suggested in the present invention may be prepared using various halogen reagents with intermediate compound (19).

Compounds as CCR2 antagonist prepared according to methods provided in reaction formula I to VI, are as in the following.

| Example | Chemical name |
|---|---|
| 1 | N-{[1-(2-(1-(phenylaminocarbonyl)-piperazine-4-yl)ethyl)-pyrrolidine-(3R)-yl-carbamoyl]-methyl}-3-trifluoromethylbenzamide, |
| 2 | N-{[1-(2-(1-(p-tolylaminocarbonyl)-piperazine-4-yl)-ethyl)-pyrrolidine-(3R)-yl-carbamoyl]-methyl}-3-trifluoromethylbenzamide, |
| 3 | N-{[1-(2-(1-(4-chlorophenylaminocarbonyl)-piperazine-4-yl)-ethyl)-pyrrolidine-(3R)-yl-carbamoyl]-methyl}-3-trifluoromethylbenzamide, |
| 4 | N-{[1-(2-(1-(methoxycarbonyl)-piperazine-4-yl)ethyl)-pyrrolidine-(3R)-yl-carbamoyl]-methyl}-3-trifluoromethylbenzamide, |
| 5 | N-{[1-(2-(1-(ethoxycarbonyl)-piperazine-4-yl)ethyl)-pyrrolidine-(3R)-yl-carbamoyl]-methyl}-3-trifluoromethylbenzamide, |
| 6 | N-{[1-(2-(4-benzoylpiperazine-1-yl)ethyl)-pyrrolidine-(3R)-yl-carbamoyl]-methyl}-3-trifluoromethylbenzamide, |
| 7 | N-{[1-(2-(4-(2-methylbenzoyl)piperazine-1-yl)ethyl)-pyrrolidine-(3R)-yl-carbamoyl]-methyl}-3-trifluoromethylbenzamide, |
| 8 | N-{[1-(2-(4-(3-methylbenzoyl)piperazine-1-yl)ethyl)-pyrrolidine-(3R)-yl-carbamoyl]-methyl}-3-trifluoromethylbenzamide, |
| 9 | N-{[1-(2-(4-(4-methylbenzoyl)piperazine-1-yl)ethyl)-pyrrolidine-(3R)-yl-carbamoyl]-methyl}-3-trifluoromethylbenzamide, |
| 10 | N-{[1-(2-(4-(4-fluorobenzoyl)piperazine-1-yl)ethyl)-pyrrolidine-(3R)-yl-carbamoyl]-methyl}-3-trifluoromethylbenzamide, |

-continued

| Example | Chemical name |
|---|---|
| 11 | N-{[1-(2-(4-(4-cyanobenzoyl)piperazine-1-yl)ethyl)-pyrrolidine-(3R)-yl-carbamoyl]-methyl}-3-trifluoromethylbenzamide, |
| 12 | N-{[1-(2-(4-(4-ethylbenzoyl)piperazine-1-yl)ethyl)-pyrrolidine-(3R)-yl-carbamoyl]-methyl}-3-trifluoromethylbenzamide, |
| 13 | N-{[1-(2-(4-(phenylsulfonyl)piperazine-1-yl)ethyl)-pyrrolidine-(3R)-yl-carbamoyl]-methyl}-3-trifluoromethylbenzamide, |
| 14 | N-{[1-(2-(4-propionylpiperazine-1-yl)ethyl)-pyrrolidine-(3R)-yl-carbamoyl]-methyl}-3-trifluoromethylbenzamide, |
| 15 | N-{[1-(2-(4-benzylpiperazine-1-yl)ethyl)-pyrrolidine-(3R)-yl-carbamoyl]-methyl}-3-trifluoromethylbenzamide, |
| 16 | N-{[1-(1-(4-benzoylpiperazine-1-yl)propane-2-yl)-pyrrolidine-(3R)-yl-carbamoyl]-methyl}-3-trifluoromethylbenzamide, |
| 17 | N-{[1-(3-(4-benzoylpiperazine-1-yl)butane-2-yl)-pyrrolidine-(3R)-yl-carbamoyl]-methyl}-3-trifluoromethylbenzamide, |
| 18 | N-{[1-(2-(4-benzoylpiperazine-1-yl)propane-1-yl)-pyrrolidine-(3R)-yl-carbamoyl]-methyl}-3-trifluoromethylbenzamide, |
| 19 | N-{[1-(1-(4-benzoylpiperazine-1-yl)butane-2-yl)-pyrrolidine-(3R)-yl-carbamoyl]-methyl}-3-trifluoromethylbenzamide, |
| 20 | N-{[1-(2-(4-benzoylpiperazine-1-yl)butyl)-pyrrolidine-(3R)-yl-carbamoyl]-methyl}-3-trifluoromethylbenzamide, |
| 21 | N-{[1-(2-(4-benzoylpiperazine-1-yl)-2-methylpropyl)-pyrrolidine-(3R)-yl-carbamoyl]-methyl}-3-trifluoromethylbenzamide, |
| 22 | N-{[1-(1-(4-benzoylpiperazine-1-yl)-2-methylpropan-2-yl)-pyrrolidine-(3R)-yl-carbamoyl]-methyl}-3-trifluoromethylbenzamide, |
| 23 | N-{[1-(3-(4-(3-chlorophenyl)piperazine-1-yl)butane-2-yl)-pyrrolidine-(3R)-yl-carbamoyl]-methyl}-3-trifluoromethylbenzamide, |
| 24 | N-{[1-(1-(4-phenylpiperazine-1-yl)propan-2-yl)-pyrrolidine-(3R)-yl-carbamoyl]-methyl}-3-trifluoromethylbenzamide, |
| 25 | N-{[1-(1-(4-cyclohexylpiperazine-1-yl)propan-2-yl)-pyrrolidine(3R)-yl-carbamoyl]-methyl}-3-trifluoromethylbenzamide, |
| 26 | N-{[1-(2-(4-(2-hydroxybutyl)piperazine-1-yl)ethyl)-pyrrolidine-(3R)-yl-carbamoyl]-methyl}-3-trifluoromethylbenzamide, |
| 27 | N-{[1-(2-(4-(2-hydroxy-2-methylpropyl)piperazine-1-yl)ethyl)-pyrrolidine-(3R)-yl-carbamoyl]-methyl}-3-trifluoromethylbenzamide, |
| 28 | N-{[1-(2-(4-(2-hydroxy-2-phenylethyl)piperazine-1-yl)ethyl)-pyrrolidine-(3R)-yl-carbamoyl]-methyl}-3-trifluoromethylbenzamide, |
| 29 | N-{[1-(2-(4-(2-(4-chlorophenyl)-2-hydroxyethyl)piperazine-1-yl)ethyl)-pyrrolidine-(3R)-yl-carbamoyl]-methyl}-3-trifluoromethylbenzamide, |
| 30 | N-{[1-(2-(4-benzoylpiperazine-1-yl)-2-oxoethyl)-pyrrolidine-(3R)-yl-carbamoyl]-methyl}-3-trifluoromethylbenzamide, |

-continued

| Example | Chemical name |
|---|---|
| 31 | N-{[1-(2-(4-(4-methylbenzoyl)piperazine-1-yl)-2-oxoethyl)-pyrrolidine-(3R)-yl-carbamoyl]-methyl}-3-trifluoromethylbenzamide, |
| 32 | N-{[1-(2-(4-(4-ethylbenzoyl)piperazine-1-yl)-2-oxoethyl)-pyrrolidine-(3R)-yl-carbamoyl]-methyl}-3-trifluoromethylbenzamide, |
| 33 | N-{[1-(2-(4-(3-methylbenzoyl)piperazine-1-yl)-2-oxoethyl)-pyrrolidine-(3R)-yl-carbamoyl]-methyl}-3-trifluoromethylbenzamide, |
| 34 | N-{[1-(2-(4-(2-methylbenzoyl)piperazine-1-yl)-2-oxoethyl)-pyrrolidine-(3R)-yl-carbamoyl]-methyl}-3-trifluoromethylbenzamide, |
| 35 | N-{[1-(2-(4-phenylpiperazine-1-yl)-2-oxoethyl)-pyrrolidine-(3R)-yl-carbamoyl]-methyl}-3-trifluoromethylbenzamide, |
| 36 | N-{[1-(2-(4-(benzoxycarbonyl)piperazine-1-yl)-2-oxoethyl)-pyrrolidine-(3R)-yl-carbamoyl]-methyl}-3-trifluoromethylbenzamide, and |
| 37 | N-{[1-(2-(4-benzoyl-2,5-dimethylpiperazine-1-yl)ethyl)-pyrrolidine-(3R)-yl-carbamoyl]-methyl}-3-trifluoromethylbenzamide |

[Pharmaceutical Use]

The various types of diseases and symptoms can be treated with compound of the present invention inhibiting activity of CCR2 receptor. More specifically they are intended to use for prevention, treatment and improvement of inflammatory diseases, disorders and symptoms CCR2 mediated. In another aspects, they are intended to use for provide inhibitory or regulatory action of CCR2 activation due to diseases and symptoms associated with MCP-1 expression or overexpression.

Those related diseases include inflammatory and autoimmune associated disease, specifically allergic rhinitis, respiratory allergic disease, chronic obstructive pulmonary disease, asthma, pneumonia, rhematic arthritis, uveitis, multiple sclerosis, contact dermatitis, atopic dermatitis, Crohn's disease, colitis and nephritis. Diabetes mellitus, diabetic complication, obesity, hyperlipidemia as metabolic diseases are also included. They are useful for arteriosclerosis and restenosis as vascular related diseases and are also used as vasoprotective agents. They are also useful as immunosuppressant to organ transplant rejection.

Meanwhile compounds provided in the present invention may be useful for all those diseases and symptoms caused by pathological role of CCR2 receptor. Therefore, use as therapeutic agent or reliever to those disease and symptoms is not defined to the described herein.

The compound provided in the present invention is active ingredients as CCR2 antagonist, which daily oral dose is 0.01 mg/kg to 1,000 mg/kg, preferably 0.1 mg to 100 mg/kg. Such dose is properly decided according to diseases and target patients. They could be administered once to five time per day according to dosage regimens and be administered on alone or combination with other drug if required.

Meanwhile the present invention relates to pharmaceutical compositions containing compounds of the formula I above.

The said pharmaceutical compositions include tablet, bubbling tablet, capsule, granule, powder, sustained release tablet, sustained release capsule. Also included are different formulations such as intravenous or intramuscular injection, suspension, suppositories, dermal patch, intraperitoneal injection, intranasal cavity transfer apparatus and they can be administered as other active ingredient formulation and pharmaceutical formulation in accordance with purpose of administration.

To prepare preferred pharmaceutical compositions having compounds provided with the present invention as active ingredients, they can be formulated including excipient, diluent, adjuvant, coating material, antioxidant, aromatic compound. Specific examples of excipient and adjuvant include gelatin, sucrose, lactose, lecithin, pectin, starch, cyclodextrin, cyclodextrin derivatives, dextran, polyvinylpyrrolidone, polyvinyl acetate, gum arabic, alginate, tilose, talc, and lycopodium, silicic acid, calcium hydrogen phosphate, cellulose, methoxypropylcellulose, methyl cellulose, hydroxypropyl methyl cellulose, hydroxypropyl methyl cellulose phthalate, saturated or unsaturated fatty acids, vegetable glycerol esters, polyglycerol esters, alcohols, polyethylene glycol, aliphatic alcohols, glycols, glycerol, diethylene glycol, propylene glycol, sorbitol, mannitol, saturated or unsaturated fatty acid esters. Specific examples of additionally usable adjuvants or disintegrants include cross-linked polyvinylpyrrolidone, sodium carboxymethyl starch, sodium carboxymethyl cellulose, micro-crystalline cellulose. Coating materials of tablet could be used, and specific examples thereof include acrylic acid, methacrylic acid, esters of methacrylic acid polymers and copolymers, Jane, ethyl cellulose, ethyl cellulose succinate, shellac, citric acid esters, tartaric esters, glycerol, glycerol esters, polyethylene glycol. Meanwhile for the preparation of the desired formulation or suspension, water or appropriate amount of organic solvent to the physiologically acceptable extent can be used. In particular, on the liquid formulation, preservatives, antioxidants, and aromatic intensifier can be useful, those concrete examples include solvate potassium, methyl 4-hydroxy benzoate, propyl 4-hydroxy benzoate, ascorbic acid, peppermint oil, etc. To make a preferred formulation if required, solubilizers and emulsifying agents such as polyvinylpyrrolidone, polysorbate 80 can be used.

To administer compound provided in the present invention to human body, the following representative, illustrative, tablet formulation as pharmaceutical method is like the following. Compound A, B and C below provided mean active ingredients for antagonism of CCR2 receptor in the present invention.

Composition 1 (unit: mg/tablet)
 Compound A: 100.00
 Lactose: 183.00
 Sodium Lauryl Sulfate (SLS): 18.00
 Polyvinylpyrrolidone (PVP): 15.00
 Sodium Croscarmellose: 18.00
 Micro-crystalline cellulose: 60.00
 Magnesium Stearate: 6.00
 Total amount: 400.00

Composition 2 (Unit: mg/tablet)
 Compound B: 200.00
 Lactose: 203.75
 Sodium Lauryl Sulfate (SLS): 15.00
 Polyvinylpyrrolidone (PVP): 12.50
 Sodium Croscarmellose: 15.00
 Micro-crystalline Cellulose: 50.00
 Magnesium Stearate: 3.75
 Total amount: 500.00

Composition 3 (Unit: mg/tablet)
 Compound C, 100.00
 Lactose: 213.00
 Sodium Lauryl Sulfate (SLS) 12.00
 Polyvinylpyrrolidone (PVP): 10.00
 Sodium Croscarmellose: 12.00
 Micro-crystalline Cellulose: 50.00
 Magnesium Stearate: 3.00
 Total amount: 400.00

[Physiological Effect]

CCR2 antagonistic effect provided with the present compound may be verified with proper physiological test. Specifically through affinity test between compounds of the present invention and CCR2 receptor proteins or unit cell, inhibitory effect on immune cell chemotaxis and $Ca^{2+}$ flux in cytoplasm could be quantitatively analyzed to determine. More specific procedure in relation to each physiological test is as in the followings.

1) CCR2 Receptor Protein Binding Assay

Affinity for compound blocking signal transduction of receptor by binding to CCR2 is observed using human recombinant CCR2 receptor (Perkinelmer, USA) expressed in CHO cell and radiolabelled ligand ($[^{125}I]$-MCP1; Perkinelmer, USA). The buffer used for receptor binding assay is 50 mM Hepes (pH 7.4) containing 5 mM $MgCl_2$, 1 mM $CaCl_2$ and 0.5% BSA. The resultant reaction mixture in final volume 0.25 ml is prepared by adding CCR2 membrane (10 μg/well), $[^{125}I]$-MCP1 to test drug in 96-well plate on $[^{125}I]$-MCP1 binding assay and is cultivated on 27° C. for 60 min.

After incubation, reaction is terminated with fast filtering through Wallac filtermat A GF/C glass fiber filter (Wallac, Finland) pre-wetted in 0.5% PEI using Inotech harvester (Inotech) and is washed in cold 50 mM Tris-HCl (pH 7.4) buffer solution. After filter is covered with MeltiLex, it is sealed in sample bag, dried on oven, and counted using MicroBeta Plus (Wallac).

The compound affinity to receptor is measured at high concentration of 10 μM. And relatively high affinity compound exhibiting inhibitory effect more than 50% in 10 μM is tested repeatedly twice times over 7-8 step concentration in each two test tube and computerized non-linear regression is used with resulting isotherm to calculate affinity to receptor ($IC_{50}$) (GraphPad Prism Program, San Diego, USA). D-Trp6-LHRH (1 μM) is used in non-specific binding measurement.

2) CCR2 Inhibitory Effect on $Ca^{2+}$ Flux

After seeding CCR2b transformed cell (HEK293/CCR2b) on black-clear bottom plate coated with lysine, it was adapted for 24 hours and exchanged into serum free media (DMEM) and allowed to cultivate overnight. Next day After the compound is treated with Flour-4 (calcium dye, Molecular probe) and cultivated for 50 min on incubator, it is washed calcium-free buffer solution and pretreated for 10-15 min. It is added with MCP-1 and its signal is measured with FlexStation$^{II}$ (Molecular device).

3) Inhibitory Effect on Chemotaxis

Antagonistic effect on the compound on CCR2 activity was measured by leukocyte chemotaxis assay using a proper cell line. The proper cell include cell line, recombinant cell or separated cell in which CCR2 is expressed and chemotaxis induced by CCR2 ligand (for example, MCP-1) is exhibited.

The used cell line is THP-1 and it is proliferated RPMI-1640 supplemented with 10% fetal calf serum under 37° C. at 5% $CO_2$ incubator. Cell density was maintained near about $0.5 \times 10^6$ cells/ml.

MCP-1 induced chemotaxis is applied to 96 well chemotaxis chamber (Neuro Probe) and reassociated hMCP-1 (10 ng/ml, R&D) or 30 μl buffer solution alone is added to lower chamber and 50 μl of THP-1 cell ($4 \times 10^6$ cells/ml) pre-cultivated for 15 min with each concentration of test compound is added to upper chamber. Cell is allowed to have chemotaxis under 37° C., 5% $CO_2$ incubator for 2 hours. After incubating for 2 hours, cells which is not moved from the upper side of filter are removed by wiping the filter with cotton swab.

The cells moved to lower chamber was measured using fluorescent plate reader under $\lambda_{excite}$=480 nm, $\lambda_{exit}$=520 nm.

The chemotaxis may be described as chemotaxis coefficient, ratio between mean value of cells moved under existence of MCP-1 and mean value of cells moved under absence of chemokine.

$$\text{Inhibition \%} = (1-((F_{sample}-F_{buffer\ solution})/(F_{MCP-1}-F_{buffer\ solution}))) \times 100 \quad \text{[Mathematical Formula 1]}$$

wherein $F_{sample}$ is fluorescence of cells pre-cultivated by test compound at each concentration and moved to lower chamber at 10 ng/ml MCP-1; $F_{MCP-1}$ is fluorescence of cells pre-cultivated by buffer solution (0.1% DMSO) and moved at 10 ng/ml; $F_{buffer\ solution}$ is fluorescence of cells precultivated by buffer solution (0.1% DMSO) and voluntarily moved to lower chamber.

Resulting from testing the following protocol of affinity to said CCR2 receptor protein, $IC_{50}$ of the compounds of the present invention is 1 nM to 10 μM range. Resulting from testing inhibitory effect protocol on the $Ca^{2+}$ flux and chemotaxis, $IC_{50}$ of the compounds of the present invention is 1 nM to 10 μM.

Meanwhile, effectiveness of the compound in relation to the present invention as active pharmaceutical ingredient may be verified by proper physiological test. Specifically toxicity as a drug may be preliminary predicted based on evaluating inhibitory level (CYP450 inhibition) to drug metabolizing enzyme to predict plural drugs interactions, evaluating binding strength to hERG $K^+$ ion channel to predict cardiac toxicity, and implementing cytotoxcity test on a number of other cell lines. More specific procedure to each physiological test is same as described below.

1) Evaluation of CYP450 Inhibitory Activity

It is analyzed inhibitory activity assay on 5 types (CYP3A4, 2C9, 2C19, 2D6, 1A2) of 11 types CYP450, drug metabolic enzyme. Luciferin detection reagent is dissolved in buffer solution and each CYP enzyme membrane is prepared.

4-fold concentration of the compound in 6.25 μl is prepared, and added to 6.25 μl mixture containing enzyme and proper different substrate depending on enzyme types, and kept for 10 min. After reacting with 12.5 μl NADPH regeneration reagent of CYP enzyme for 30 min, adding 25 μl luciferin detection reagent and keeping for 20 min, luminescence is measured at Fusion α.

In evaluating said CYP450 inhibitory activity, it is found that such activity is relatively lower since the compounds provided in the present invention as a CCR2 antagonis exhibit binding strength of the range lower than 50% under 10 μM compound concentration.

2) Evaluation of hERG $K^+$ on Cardiotoxicity

The hERG $K^+$ ion channel binding strength of drug is evaluated by radiolabelled ligand $[^3H]$Astemizole substitution method. Drug is added to buffer solution containing hERG cell membrane (2.5 μg/well), $[^3H]$-Astemizole (4 nM) to make a reaction mixture and react at room temperature for 60 min.

After it is rapidly filtered with Filtermat-A (Wallac) filter pre-wetted within 0.3% polyethyleneimine by harvester (Inotech) and washed. The filter is covered with MeltiLex, sealed within sample bag, and dried. RI value is measured with MicroBeta Plus (Wallac). The degree of binding inhibition ($IC_{50}$) is calculated by non-linear regression analysis (GraphPad Prism Program) for inhibitory activity and non-specific binding assay is performed through 0.1 μM astemizole.

Resulting from said hERG $K^+$ cardiotoxicity test to compounds as CCR2 antagonist described in the present invention, those compounds show little cardiotoxicity and safe since the compounds exhibit binding strength of the range lower than 50% under 10 μM of the compound concentration.

3) Cytotoxicity (Cell Viability)

The MTS (3-(4,5-dimethylthiazol-2-yl)-5-(3-carboxymethoxyphenyl)-2-(4-sulfophenyl)-2H-tetrazolium, inner salt, Promega, U.S.A) assay to THP-1 cell is used to measure cytotoxicity of test compound. The MTS assay is applicable to sensitively measure viability, multiplication and activity of cell and is a method using transformation the yellow MTS into insoluble formazan by dehydrogenase of mitochondria during metabolism of viable cell. The THP-1 cell is proliferated on RPMI-1640 supplemented with 10% fetal bovine serum under 37° C., at 5% $CO_2$ incubator. Cell density is maintained around $0.5 \times 10^6$ cells/ml. THP-1 cell is poured into 96-well plate in $1 \times 10^6$ cell/ml and treating with 1, 10 μM concentration of test compound, after 24 hours 20 μl of 317 μg/ml MTS is treated to 96-well plate. Cell viability as the he absorbance of crystalline formazan of test group to control group observed at 490 nm using ELISA reader after 1 hour is calculated by following mathematical formula 2.

Cell viability(%)=(Absorbance of experimental wells)/(Absorbance of control wells))×100  [Mathematical Formula 2]

The cell cytotoxicity test is performed to many cell lines, for example HepG2, NIH3T3, CHO-K1, HEK293, in addition to THP-1 illustrated above, and test procedures related to these are same or similar as described method above. Resulting from cytotoxicity measurement to test compound, cell viability of test group treated with 10 μM of test compound compared to the control group without treatment to all cell line was more than 50%, which means it shows little cytotoxicity and is expected to be safe compound.

The test results to the compounds of the present invention are described as illustration in the following Table 2 according to physiological test protocol above.

TABLE 2

| Physiological test | Example 6 compound | Example 7 compound |
|---|---|---|
| Affinity to CCR2 receptor, $IC_{50}$ (μM) | 0.99 | 4.44 |
| Blocking $Ca^{2+}$ flux, $IC_{50}$ (μM) | 0.018 | 0.12 |
| Inhibition of Chemotaxis, $IC_{50}$ (μM) | 0.009 | 0.070 |
| Inhibition of CYP450, % @10 μM: | | |
| 3A4 | 6.5 | 28.2 |
| 2C9 | 23.6 | 19.0 |
| 2C19 | 14.2 | 9.5 |
| 2D6 | 8.5 | -3.5 |
| 1A2 | 23.5 | 6.6 |
| Cell viability, % @10 μM: | | |
| HepG2 | 73.5 | 105.8 |
| NIH 3T3 | 70.6 | 73.0 |
| CHO-K1 | 84.6 | 80.1 |
| HEK 293 | 59.3 | 66.9 |

Meanwhile intermediates according to the described method as following manufacturing example may be used to synthesize compound as CCR2 antagonist of the present invention.

Manufacturing Example 1

(3-trifluoromethylbenzoylamino)-acetic acid

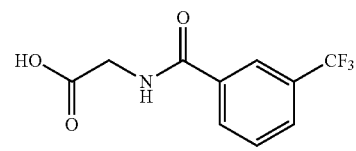 [SMILES: O=C(O)CNC(=O)c1cccc(C(F)(F)F)c1]

Glycine 0.763 g (10.16 mmol) was suspended into acetonitrile 20 ml and 2M NaOH aqueous solution 12.7 ml (25.40 mmol, 2.5 eq.) was also added. After chilling at 0-3° C., 2.12 g (10.16 mmol, 1.0 eq.) of 3-(trifluoromethyl)-benzoyl chloride was diluted with 4 ml acetonitrile and was added dropwise slowly to reaction mixture. After one hour agitation at same temperature, pH was controlled to 2 to 3 with 3N hydrochloric acid aqueous solution. After keeping upright at room temperature, upper organic solution was separated, and lower aqueous solution was extracted with ethylacetate three times. Those organic solution obtained as above was brought all together, dried with anhydrous magnesium sulfate and concentrated removing its solvent under decompression. Residues was solidified with tolene, filtered, washed with normal hexane and 2.28 g (91%) target compound as white solid was yielded.

$^1$H NMR (400 MHz, DMSO-$d_6$) 3.94 (2H, d), 7.74 (1H, t), 7.93 (1H, d), 8.16 (1H, d), 8.20 (1H, s), 9.12 (1H, t)

Manufacturing Example 2

N-[(1-benzylpyrrolidine-(3R)-yl-carbamoyl)-methyl]-3-trifluoromethylbenzamide

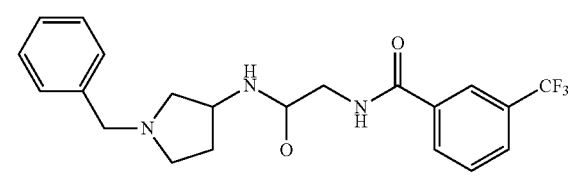 [SMILES: O=C(NCC(O)NC1CCN(Cc2ccccc2)C1)c1cccc(C(F)(F)F)c1]

10.74 g (43.4 mmol)(3-trifluoromethylbenzoylamino)-acetic acid and 6.58 g (65.10 mmol, 1.5 eq.) N-methylmorpholine described at manufacturing example 1 dissolved into 80 ml tetrahydrofuran under argon gas. After cooling at −10° C., 7.11 g (52.08 mmol, 1.2 eq.) of isobutylchloroformate was diluted with 10 ml tetrahydrofuran and was added dropwise slowly into reaction solution. It was stirred at the same temperature and 8.03 g (45.57 mmol, 1.1 eq.) (3R)-(−)-1-benzyl-3-aminopyrrolidine was diluted with 10 ml tetrahydrofuran and was added dropwise slowly. After mixing at −10° C. for one hour, 100 ml purified water was added. It was three times continuously extracted with 100 ml ethyl acetate and organic layer was recovered. It was dried with anhydrous magnesium sulfate, decompressed and concentrated. After residues are solidified with t-butylmethylether and filtered, 12.18 g (69%) target compound as white solid was yielded.

$^1$H NMR (400 MHz, DMSO-$d_6$) 1.62-1.66 (1H, m), 2.26-2.36 (2H, m), 2.54-2.59 (1H, m), 2.63-2.66 (1H, m), 2.89-2.93 (1H, m), 3.62 (2H, d), 4.10 (2H, d), 4.46-4.90 (1H, m), 6.45 (1H, br s), 7.15 (1H, br s), 7.29-7.34 (5H, m), 7.59 (1H, t), 7.78 (1H, d), 8.00 (1H, d), 8.11 (1H, s)

Manufacturing Example 3

N-(pyrrolidine-(3R)-yl-carbamoylmethyl)-3-trifluoromethylbenzamide

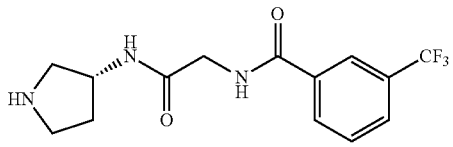 [SMILES: O=C(CNC(=O)c1cccc(C(F)(F)F)c1)N[C@@H]1CCNC1]

9.00 g (22.20 mmol) N-[(1-benzylpyrrolidine-(3R)-yl-carbamoyl)-methyl]-3-trifluoromethylbenzamide described at manufacturing example 2 was dissolved into 45 ml methanol and 0.05 g Pd(OH)$_2$ (amount of catalyst) was added. Reaction solution was stirred overnight at room temperature under 1 atmospheric pressure. Reaction solution was filtered with diatomite, the filtrate was recovered, decompressed and concentrated. The obtained residues were purified by chromatography on silicagel (mobile phase: methanol) and 5.74 g (82%) target compound as white solid was yielded.

$^1$H NMR (400 MHz, DMSO-$d_6$) 1.47-1.52 (1H, m), 1.86-1.91 (1H, m), 2.68-2.74 (1H, m), 2.79-2.84 (1H, m), 2.86-2.91 (1H, m), 3.16 (2H, s), 3.86 (2H, d), 4.05-4.13 (1H, m), 7.73 (1H, t), 7.93 (1H, d), 8.00 (1H, d), 8.17 (1H, d), 8.22 (1H, s), 8.98 (1H, t)

Manufacturing Example 4

N-{[1-(2-(4-tert-butoxycarbonylpiperazine-1-yl)ethyl)-pyrrolidine-(3R)-yl-carbamoyl]-methyl}-3-trifluoromethylbenzamide

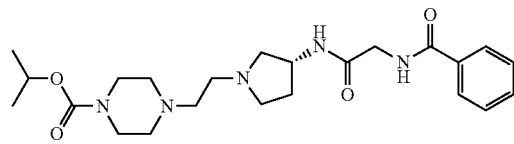

1.00 g (3.17 mmol) N-(pyrrolidine-(3R)-yl-carbamoylmethyl)-3-trifluoromethylbenzamide and 1.32 g (9.52 mmol, 3.0 eq.) potassium carbonate described at manufacturing example 3 were added into 25 ml acetonitrile and 0.98 g (3.17 mmol, 1.0 eq.) tert-butyl 4-(2-(methylsulfonyloxy)ethyl)piperazine-1-carboxylate diluted with 5 ml acetonitrile was added dropwise slowly at room temperature. After heating from room temperature to 80° C. and mixing for 24 hours, 25 ml purified water was added and the reaction solution was extracted with 25 ml ethyl acetate three times. After organic layer was brought together, dried with anhydrous magnesium sulfate, residues obtained by decompressed concentration were purified by chromatography on silicagel phase (mobile phase: dichloromethane/methanol=10:1) and 1.14 g (68%) target compound as white solid was yielded.

$^1$H NMR (400 MHz, CDCl$_3$) 1.45 (9H, s), 1.64-1.72 (1H, m), 2.28-2.80 (12H, m), 2.95-3.04 (1H, m), 3.36-3.52 (4H, m), 4.07-4.13 (2H, m), 4.47-4.52 (1H, m), 6.73-6.84 (1H, m), 7.28-7.32 (1H, m), 7.58 (1H, t), 7.77 (1H, d), 8.02 (1H, d), 8.12 (1H, s)

Manufacturing Example 5

N-{[1-(2-(piperazine-1-yl)ethyl)-pyrrolidine-(3R)-yl-carbamoyl]-methyl}-3-trifluoromethylbenzamide hydrochloride

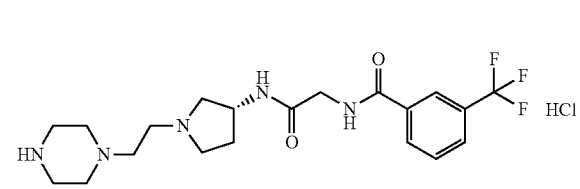 [SMILES: O=C(CNC(=O)c1cccc(C(F)(F)F)c1)N[C@@H]1CCN(CCN2CCNCC2)C1 ; Cl]

0.65 g (1.23 mmol) N-{[1-(2-(4-tert-butoxycarbonylpiperazine-1-yl)ethyl)-pyrrolidine-(3R)-yl-carbamoyl]-methyl}-3-trifluoromethylbenzamide described at manufacturing example 4 was dissolved with 3 ml ethanol saturated with hydrochloric acid. After mixing for 1.5 hour at room temperature and decompressed concentration and dried overnight under high vacuum, 0.56 g (98%) target compound as yellow syrup was yielded.

MS (M+1)$^+$: 428.4

Manufacturing Example 6

N-{[1-(2-hyroxypropyl)-pyrrolidine-(3R)-yl-carbamoyl]-methyl}-3-trifluoromethylbenzamide

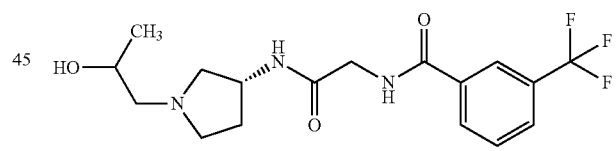

200 mg (0.63 mmol) N-(pyrrolidine-(3R)-yl-carbamoylmethyl)-3-trifluoromethylbenzamide described at manufacturing example 3 and calcium carbonate 263 mg (1.90 mmol, 3.0 eq.) was suspended into 10 ml acetonitrile at room temperature. After 122 mg (2.09 mmol, 3.0 eq.) propylene oxide was added, heating with reflux and was stirred overnight. After cooling to room temperature and 15 ml purified water was added, and the reaction solution was extracted twice with 15 ml ethylacetate. After organic layer was collected, dried with anhydrous magnesium sulfate, and concentrated with decompression. The obtained residues were purified (mobile phase: dichloromethane/methanol=5:1) by silicagel chromatography, 154 mg (65%) target compound as yellow solid was yielded.

$^1$H NMR (400 MHz, DMSO-$d_6$) 1.02 (3H, d), 1.48-1.59 (1H, m), 2.00-2.10 (1H, m), 2.22-2.40 (4H, m), 2.50-2.58 (2H, m), 3.15 (2H, d), 3.60-3.71 (1H, m), 3.85 (2H, d), 4.08-

4.20 (2H, m), 4.30 (1H, t), 7.73 (1H, t), 7.91 (1H, d), 8.05-8.12 (1H, m), 8.16 (1H, d), 8.21 (1H, s), 8.95-9.01 (1H, m)

Manufacturing Example 7

N-{[1-(2-hydroxybutyl)-pyrrolidine-(3R)-yl-carbamoyl]-methyl}-3-trifluoromethylbenzamide

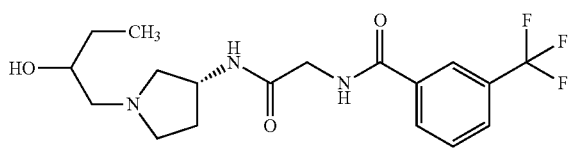 [SMILES: CCC(O)CN1CC[C@@H](NC(=O)CNC(=O)c2cccc(C(F)(F)F)c2)C1]

110 mg (45%) target compound as yellow liquid was yielded using same method as manufacturing example 6 with 200 mg (0.63 mmol) N-(pyrrolidine-(3R)-yl-carbamoylmethyl)-3-trifluoromethylbenzamide described at manufacturing example 3, 263 mg (1.90 mmol, 3.0 eq.) potassium carbonate and 229 mg (3.17 mmol, 5.0 eq.) 1,2-epoxybutane.

$^1$H NMR (400 MHz, DMSO-$d_6$) 0.85 (3H, t), 1.40-1.60 (2H, m), 2.00-2.10 (1H, m), 2.30-2.42 (4H, m), 2.59-2.69 (2H, m), 3.85 (2H, d), 4.08 (2H, q), 4.11-4.20 (1H, m), 4.22 (1H, t), 7.73 (1H, t), 7.91 (1H, d), 8.07 (1H, d), 8.16 (1H, d), 8.21 (1H, s), 8.96 (1H, t)

Manufacturing Example 8

N-{[1-(2-hydroxy-2-methylpropyl)-pyrrolidine-(3R)-yl-carbamoyl]-methyl}-3-trifluoromethylbenzamide

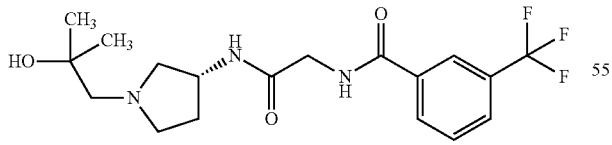

700 mg (57%) target compound as yellow liquid was yielded using same method as manufacturing example 6 with 1.00 g (3.17 mmol) N-(pyrrolidine-(3R)-yl-carbamoylmethyl)-3-trifluoromethylbenzamide described at manufacturing example 3, 1.32 g (9.55 mmol, 3.0 eq.) potassium carbonate and 690 mg (9.57 mmol, 3.0 eq.) isobutylene oxide. $^1$H NMR (400 MHz, DMSO-$d_6$) 1.08 (6H, s), 1.50-1.60 (1H, m), 1.99-2.09 (1H, m), 2.28-2.37 (2H, m), 2.45-2.53 (2H, m), 2.69-2.80 (2H, m), 3.88 (2H, d), 4.05 (1H, s), 4.11-4.20 (1H, m), 7.74 (1H, t), 7.92 (1H, d), 8.04 (1H, d), 8.18 (1H, d), 8.23 (1H, s), 8.99 (1H, t)

Manufacturing Example 9

(4-(2-hydroxy-2-methylpropyl)piperazine-1-yl)phenylmethanone

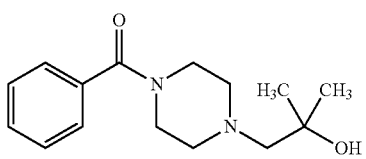 [SMILES: CC(C)(O)CN1CCN(C(=O)c2ccccc2)CC1]

500 mg (2.63 mmol) 1-benzoylpiperazine and 1.10 g (7.96 mmol, 3.0 eq.) potassium carbonate were suspended to 20 ml acetonitrile at room temperature. After adding 570 mg (7.90 mmol, 3.0 eq.) isobutylene oxide, it was heated at reflux and stirred overnight. After cooling to room temperature and adding 30 ml purified water, it was extracted twice with 30 ml ethylacetate. After collecting organic layer and drying with anhydrous magnesium sulfate, it was concentrated with decompression. The obtained residue was purified by chromatography using silicagel (mobile phase: dichloromethane/methanol=20:1) and 276 mg (40%) target compound as light-yellow solid was yielded.

$^1$H NMR (400 MHz, DMSO-$d_6$) 1.10 (6H, s), 2.23 (2H, s), 2.43-2.52 (2H, m), 2.53-2.62 (2H, m), 3.35-3.45 (2H, m), 3.55-3.65 (2H, m), 4.13 (1H, s), 7.35-7.38 (2H, m), 7.43-7.46 (3H, m)

Manufacturing Example 10

1-(4-benzoylpiperazine-1-yl)propan-2-one

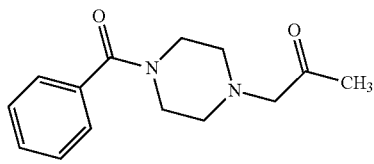 [SMILES: CC(=O)CN1CCN(C(=O)c2ccccc2)CC1]

0.10 g (0.53 mmol) 1-benzoylpiperazine and potassium carbonate 0.22 g (1.58 mmol, 3.0 eq.) were added to 5 ml acetonitrile and 0.05 g (0.53 mmol, 1.0 eq.) chloroacetone was added dropwise slowly at room temperature. After mixing for one hour, 5 ml purified water was added, and the reaction mixture was extracted with 10 ml ethylacetate three times. After collecting organic layer, drying with anhydrous magnesium sulfate, and concentrating with decompression, residues obtained were purified with silicagel chromatography (mobile phase: dichloromethane/methnol=10:1) and 0.11 g (83%) target compound as yellow serup were yielded.

$^1$H NMR (400 MHz, CDCl$_3$) 2.18 (3H, s), 2.41-2.69 (4H, m), 3.27 (2H, s), 3.42-3.54 (2H, m), 3.81-3.93 (2H, m), 7.40-7.46 (5H, m)

Manufacturing Example 11

3-(4-benzoylpiperazine-1-yl)butane-2-one

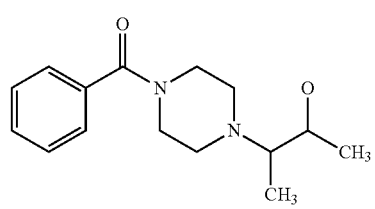 [SMILES: CC(O)C(C)N1CCN(C(=O)c2ccccc2)CC1]

0.05 g (73%) target compound as yellow syrup was yielded on the same method as manufacturing example 10 using 0.05 g (0.26 mmol) 1-benzoylpiperazine, 0.11 g (0.79 mmol, 3.0 eq.) potassium carbonate, 0.03 g (0.26 mmol, 1.0 eq.) 3-chloro-2-butanon.

$^1$H NMR (400 MHz, CDCl$_3$) 1.17 (3H, d), 2.25 (3H, s), 2.38-2.72 (4H, m), 3.20 (1H, q), 3.38-3.53 (2H, m), 3.74-3.89 (2H, m), 7.40-7.48 (5H, m)

Manufacturing Example 12 tert-butyl 4-(2-chloroacetyl)piperazine-1-carboxylate

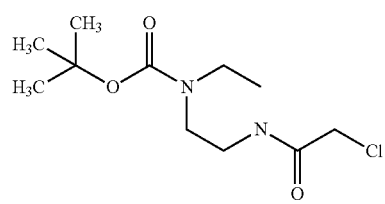 [SMILES: CCN(CCNC(=O)CCl)C(=O)OC(C)(C)C]

2.00 g (10.74 mmol) tert-butyl 1-piperazinecarboxylate, 1.30 g (12.89 mmol, 1.2 eq.) triethylamine were dissolved into 25 ml dichloromethan under argon gas. After cooling to 3° C., 1.33 g (11.81 mmol, 1.1 eq.) chloroacetyl chloride was diluted with 5 ml dichloromethane and added dropwise slowly into reaction solution. After stirring at 3° C. for 1 hour, 20 ml purified water was added, organic layer was separated and aqueous layer was extracted once with 40 ml dichloromethane again. Organic layer was collected, dried with magnesium sulfate and concentrated with decompression. Purifying residues by chromatography using silicagel, 2.00 g (71%) target compound as yellow syrup was yielded.

$^1$H-NMR (400 MHz, CDCl$_3$) 1.48 (9H, s), 3.45 (2H, t), 3.51 (4H, s), 3.61 (2H, t), 4.09 (2H, s)

Manufacturing Example 13

N-{[1-(2-(4-tert-butoxycarbonylpiperazine-1-yl)-2-oxo-ethyl)-pyrrolidine-(3R)-yl-carbamoyl]-methyl}-3-trifluoromethylbenzamide

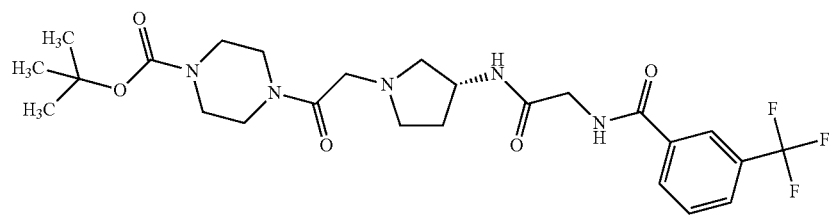 [SMILES: CC(C)(C)OC(=O)N1CCN(C(=O)CN2CC[C@@H](NC(=O)CNC(=O)c3cccc(C(F)(F)F)c3)C2)CC1]

1.00 g (3.17 mmol) N-(pyrrolidine-(3R)-yl-carbamoylmethyl)-3-trifluoromethylbenzamide described at manufacturing example 3 and 1.32 g (9.52 mmol, 3.0 eq.) potassium carbonate were added into 25 ml acetonitrile and 0.83 g (3.17 mmol, 1.0 eq.) tert-butyl 4-(2-chloroacetyl)piperazine-1-carboxylate described at manufacturing example 12 was diluted with 5 ml acetonitrile and was added dropwise slowly at room temperature into reaction mixture. After heating from room temperature to 80° C. and stirring for 2 hours, 25 ml purified water was added and the reaction mixture was extracted with 25 ml ethylacetate three times. After collecting organic layer, drying with anhydrous magnesium sulfate, and concentrating with decompression, 1.12 g (65%) target compound as white solid was yielded by purifying residues with chromatography on silicagel (mobile phase: dichloromethane/methanol=10:1).

$^1$H NMR (400 MHz, CDCl$_3$) 1.48 (9H, s), 1.72-1.81 (1H, m), 2.17-2.29 (1H, m), 2.52-2.62 (1H, m), 2.73-2.82 (1H, m), 2.85-2.95 (1H, m), 3.00 (1H, q), 3.39 (2H, d), 3.40-3.46 (4H, m), 3.47-3.55 (4H, m), 4.11-4.23 (2H, m), 4.46-4.52 (1H, m), 7.27-7.36 (1H, m), 7.44 (1H, d), 7.59 (1H, t), 7.77 (1H, d), 8.03 (1H, d), 8.13 (1H, s)

Manufacturing Example 14

N-{[1-(2-(piperazine-1-yl)-2-oxo-ethyl)-pyrrolidine-(3R)-yl-carbamoyl]-methyl}-3-trifluoromethylbenzamide hydrochloride

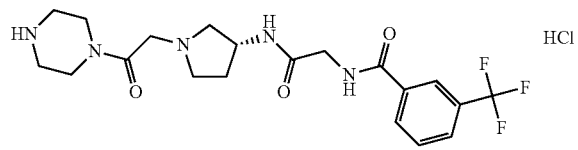 [SMILES: O=C(CNC(=O)c1cccc(C(F)(F)F)c1)N[C@@H]1CCN(CC(=O)N2CCNCC2)C1 ; Cl]

1.12 g (2.07 mmol) N-{[1-(2-(4-tert-butoxycarbonylpiperazine-1-yl)-2-oxo-ethyl)-pyrrolidine-(3R)-yl-carbamoyl]-methyl}-3-trifluoromethylbenzamide described at manufacturing example 13 was dissolved into 5 ml ethanol saturated with hydrochloric acid. After stirring for 1.5 hour at room temperature, decompression, concentration, and drying overnight under high vacuum condition, 0.93 g (94%) target compound as yellow syrup was yielded.

MS (M+1)$^+$ 478.7

The present invention was more specifically illustrated by following example. But range of the present invention was not defined with such illustration.

EXAMPLE

Example 1

N-{[1-(2-(1-(phenylaminocarbonyl)-piperazine-4-yl)ethyl)-pyrrolidine-(3R)-yl-carbamoyl]-methyl}-3-trifluoromethylbenzamide

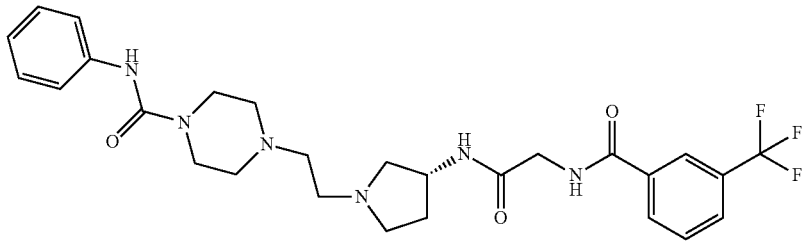 [SMILES: O=C(CNC(=O)c1cccc(C(F)(F)F)c1)N[C@@H]1CCN(CCN2CCN(C(=O)Nc3ccccc3)CC2)C1]

50 mg (0.11 mmol) N-{[1-(2-(piperazine-1-yl)ethyl)-pyrrolidine-(3R)-yl-carbamoyl]-methyl}-3-trifluoromethylbenzamide hydrochloride described at manufacturing example 5, 40 mg (0.32 mmol, 3.0 eq.) N,N-diisopropylethylamine and 10 mg (0.11 mmol, 1.0 eq.) phenyl isocianate were dissolved into 5 ml dichloromethane under argon gas. After stirring for 2 hours at room temperature, adding with purified water 10 ml and separating organic layer, aqueous layer was extracted once with 10 ml dichloromethane again. Organic layer was collected, dried with anhydrous magnesium sulfate and it was concentrated with decompression. 50 mg (67%) target compound as white solid was yielded by purifying residues with chromatography using silicagel (mobile phase: dichloromethane/methanol=10:1).

$^1$H NMR (400 MHz, CDCl$_3$) 1.67-1.78 (1H, m), 2.28-2.40 (2H, m), 2.48-2.59 (7H, m), 2.60-2.78 (2H, m), 2.84 (1H, d), 3.03-3.12 (1H, m), 3.45-3.57 (4H, m), 4.05-4.20 (2H, m), 4.47-4.52 (1H, m), 6.60 (1H, s), 7.05 (1H, d), 7.23 (2H, d), 7.32 (1H, d), 7.32-7.36 (1H, m), 7.58 (1H, t), 7.77 (1H, d), 8.01 (1H, d), 8.11 (1H, s)

Example 2

N-{[1-(2-(1-(p-tolylaminocarbonyl)-piperazine-4-yl)-ethyl)-pyrrolidine-(3R)-yl-carbamoyl]-methyl}-3-trifluoromethylbenzamide

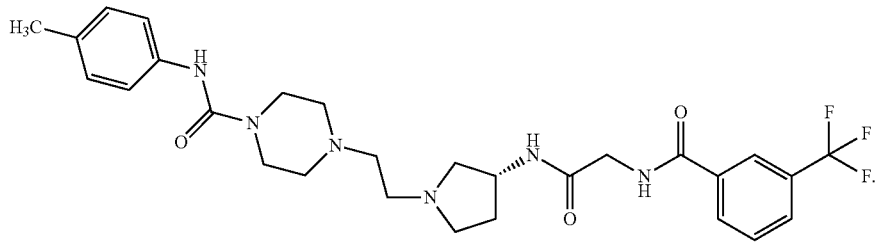 [SMILES: Cc1ccc(NC(=O)N2CCN(CCN3CC[C@@H](NC(=O)CNC(=O)c4cccc(C(F)(F)F)c4)C3)CC2)cc1]

45 mg (75%) target compound as white solid was yielded on the same method as described at example 1 using 50 mg (0.11 mmol) N-{[1-(2-(piperazine-1-yl)ethyl)-pyrrolidine-(3R)-yl-carbamoyl]-methyl}-3-trifluoromethylbenzamide hydrochloride described at manufacturing example 5, 40 mg (0.32 mmol, 3.0 eq.) N,N-diisopropylethylamine, and 14 mg (0.11 mmol, 1.0 eq.) isocyanate m-tolylester.

$^1$H NMR (400 MHz, CDCl$_3$) 1.63-1.75 (1H, m), 2.23-2.30 (2H, m), 2.32 (3H, s), 2.51-2.60 (7H, m), 2.62-2.73 (2H, m), 2.79 (1H, d), 3.02 (1H, t), 3.51 (4H, t), 4.08-4.15 (2H, m), 4.47-4.55 (1H, m), 6.37 (1H, s), 6.74 (1H, d), 6.86 (1H, d), 7.11 (1H, d), 7.14-7.21 (2H, m), 7.23 (1H, s), 7.59 (1H, t), 7.78 (1H, d), 8.01 (1H, d), 8.11 (1H, s)

Example 3

N-{[1-(2-(1-(4-chlorophenylaminocarbonyl)-piperazine-4-yl)-ethyl)-pyrrolidine-(3R)-carbamoyl]-methyl}-3-trifluoromethylbenzamide

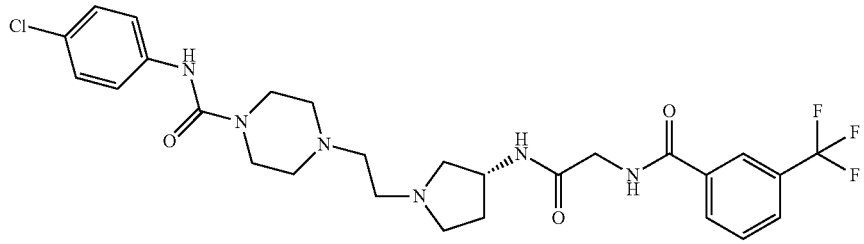 [SMILES: O=C(CNC(=O)c1cccc(C(F)(F)F)c1)N[C@@H]1CCN(CCN2CCN(C(=O)Nc3ccc(Cl)cc3)CC2)C1]

50 mg (83%) target compound as white solid was yielded the same method as described at example 1 using 50 mg (0.11 mmol) N-{[1-(2-(piperazine-1-yl)ethyl)-pyrrolidine-(3R)-yl-carbamoyl]-methyl}-3-trifluoromethylbenzamide hydrochloride described at manufacturing example 5, 40 mg (0.32 mmol, 3.0 eq.) N,N-diisopropylethylamine, and 17 mg (0.11 mmol, 1.0 eq.) isocyanate 4-chlorophenyl ester.

$^1$H NMR (400 MHz, CDCl$_3$) 1.67-1.78 (1H, m), 2.28-2.40 (2H, m), 2.48-2.59 (7H, m), 2.60-2.78 (2H, m), 2.84 (1H, d), 3.03-3.12 (1H, m), 3.45-3.57 (4H, m), 4.05-4.20 (2H, m), 4.47-4.52 (1H, m), 6.60 (1H, s), 7.05 (1H, d), 7.23 (2H, d), 7.32 (1H, d), 7.33-7.36 (1H, m), 7.58 (1H, t), 7.77 (1H, d), 8.01 (1H, d), 8.11 (1H, s)

Example 4

N-{[1-(2-(1-(methoxycarbonyl)-piperazine-4-yl)ethyl)-pyrrolidine-(3R)-yl-carbamoyl]-methyl}-3-trifluoromethylbenzamide

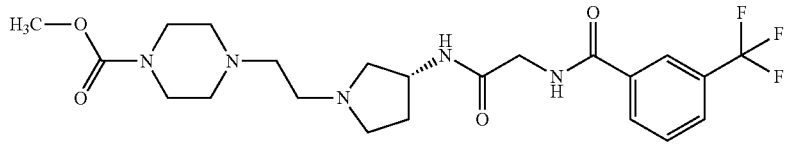 [SMILES: COC(=O)N1CCN(CCN2CC[C@@H](NC(=O)CNC(=O)c3cccc(C(F)(F)F)c3)C2)CC1]

After 50 mg (0.11 mmol) N-{[1-(2-(piperazine-1-yl)ethyl)-pyrrolidine-(3R)-yl-carbamoyl]-methyl}-3-trifluoromethylbenzamide hydrochloride described at manufacturing example 5 and 60 mg (0.43 mmol, 4.0 eq.) potassium carbonate were suspended into 3 ml acetonitrile at room temperature, 10 mg (0.11 mmol, 1.0 eq.) methyl chloroformate were diluted into 1 ml acetonitrile and slowly added. After heating with reflux and stirring for one hour, and reaction mixture was concentrated with decompression. After adding 10 ml purified water to obtained residues, it was extracted twice with 10 ml ethylacetate. Organic layer was collected, dried with anhydrous magnesium sulfate, it was concentrated with decompression. The obtained residues were purified by chromatography using silicagel (mobile phase: dichloromethane/methanol=5:1) and 40 mg (80%) target compound as light-white solid were yielded.

¹H NMR (400 MHz, CDCl₃) 1.68-1.79 (1H, m), 2.29-2.40 (2H, m), 2.41-2.49 (4H, m), 2.53-2.57 (2H, m), 2.58-2.64 (1H, m), 2.68-2.77 (2H, m), 2.80-2.91 (1H, m), 3.05-3.17 (1H, m), 3.44-3.56 (4H, m), 3.70 (3H, s), 4.06-4.18 (2H, m), 4.47-4.58 (1H, m), 6.62-6.84 (1H, m), 7.12-7.21 (1H, m), 7.60 (1H, t), 7.78 (1H, d), 8.04 (1H, d), 8.13 (1H, s)

Example 5

N-{[1-(2-(1-(ethoxycarbonyl)-piperazine-4-yl)ethyl)-pyrrolidine-(3R)-yl-carbamoyl]-methyl}-3-trifluoromethylbenzamide

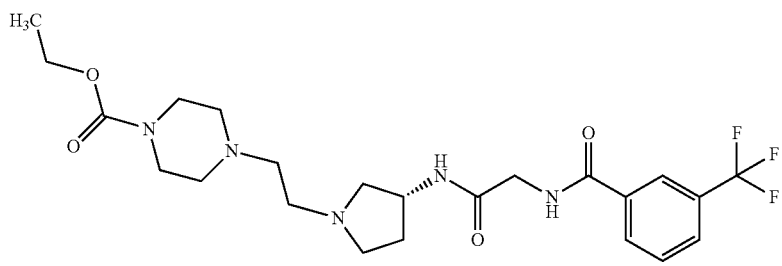 [SMILES: CCOC(=O)N1CCN(CCN2CC[C@@H](NC(=O)CNC(=O)c3cccc(C(F)(F)F)c3)C2)CC1]

40 mg (74%) target compound as white solid was yielded on the same method as example 4 using 50 mg (0.11 mmol) N-{[1-(2-(piperazine-1-yl)ethyl)-pyrrolidine-(3R)-yl-carbamoyl]-methyl}-3-trifluoromethylbenzamide hydrochloride described as manufacturing example 5, 60 mg (0.43 mmol, 4.0 eq.) potassium carbonate, and 10 mg (0.11 mmol, 1.0 eq.) ethyl chloroformate.

¹H NMR (400 MHz, CDCl₃) 1.26 (3H, t), 1.63-1.78 (1H, m), 2.23-2.38 (2H, m), 2.41-2.49 (4H, m), 2.50-2.57 (2H, m), 2.58-2.73 (3H, m), 2.80 (1H, d), 2.97-3.08 (1H, m), 3.42-3.53 (4H, m), 4.11-4.20 (4H, m), 4.48-4.53 (1H, m), 7.17 (1H, d), 7.41-7.48 (1H, m), 7.57 (1H, t), 7.76 (1H, d), 8.02 (1H, d), 8.12 (1H, s)

Example 6

N-{[1-(2-(4-benzoylpiperazine-1-yl)ethyl)-pyrrolidine-(3R)-yl-carbamoyl]-methyl}-3-trifluoromethylbenzamide

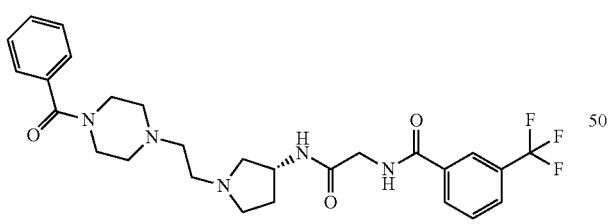

80 mg (70%) target compound as white solid was yielded on the same method as example 4 using 100 mg (0.22 mmol) N-{[1-(2-(piperazine-1-yl)ethyl)-pyrrolidine-(3R)-yl-carbamoyl]-methyl}-3-trifluoromethylbenzamide hydrochloride described at manufacturing example 5, 120 mg (0.86 mmol, 4.0 eq.) potassium carbonate, and 30 mg (0.22 mmol, 1.0 eq.) benzoyl chloride.

¹H NMR (400 MHz, CDCl₃) 1.57-1.72 (1H, m), 2.08-2.21 (1H, m), 2.22-2.36 (2H, m), 2.37-2.46 (1H, m), 2.48-2.67 (8H, m), 2.89 (1H, t), 3.36-3.52 (2H, m), 3.71-3.88 (2H, m), 4.11 (2H, d), 4.37-4.51 (1H, m), 6.64 (1H, d), 7.32-7.47 (6H, m), 7.58 (1H, t), 7.77 (1H, d), 8.00 (1H, d), 8.11 (1H, s)

MS (M+1)⁺ 532.2

Example 7

N-{[1-(2-(4-(2-methylbenzoyl)piperazine-1-yl)ethyl)-pyrrolidine-(3R)-yl-carbamoyl]-methyl}-3-trifluoromethylbenzamide

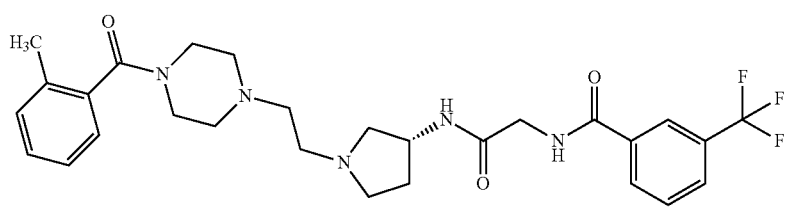 [SMILES: Cc1ccccc1C(=O)N1CCN(CCN2CC[C@@H](NC(=O)CNC(=O)c3cccc(C(F)(F)F)c3)C2)CC1]

After 50 mg (0.11 mmol) N-{[1-(2-(piperazine-1-yl)ethyl)-pyrrolidine-(3R)-yl-carbamoyl]-methyl}-3-trifluoromethylbenzamide hydrochloride described at manufacturing example 5 and 60 mg (0.43 mmol, 4.0 eq.) potassium carbonate were diluted with 3 ml acetonitrile at room temperature, 18 mg (0.12 mmol, 1.1 eq.) o-toluoyl chloride was diluted into 1 ml acetonitrile and added slowly. After heating with reflux and stirring for one hour, reaction mixture was concentrated with decompression. After adding 10 ml purified water to obtained residues, it was extracted twice with 10 ml ethylacetate. Collecting organic layer and drying with anhydrous magnesium sulfate, it was concentrated with decompression. 42 mg (71%) target compound as light-white solid was yielded by purifying obtained residues with chromatography using silicagel (mobile phase: dichloromethane/methanol=5:1).

$^1$H NMR (400 MHz, DMSO-$d_6$) 1.50-1.60 (1H, m), 2.00-2.10 (1H, m), 2.19 (3H, s), 2.22-2.55 (10H, m), 2.60-2.70 (2H, m), 3.07-3.11 (2H, m), 3.58-3.66 (2H, m), 3.84 (2H, d), 4.10-4.19 (1H, m), 7.11 (1H, d), 7.19-7.31 (3H, m), 7.72 (1H, t), 7.91 (1H, d), 8.11-8.18 (2H, m), 8.21 (1H, s), 8.99 (1H, t)

Example 8

N-{[1-(2-(4-(3-methylbenzoyl)piperazine-1-yl)ethyl)-pyrrolidine-(3R)-yl-carbamoyl]-methyl}-3-trifluoromethylbenzamide

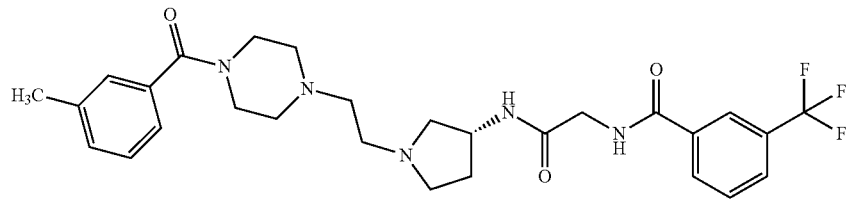 [SMILES: Cc1cccc(C(=O)N2CCN(CCN3CC[C@@H](NC(=O)CNC(=O)c4cccc(C(F)(F)F)c4)C3)CC2)c1]

45 mg (77%) target compound as yellow solid was yielded on the same method as example 7 using 50 mg (0.11 mmol) N-{[1-(2-(piperazine-1-yl)ethyl)-pyrrolidine-(3R)-yl-carbamoyl]-methyl}-3-trifluoromethylbenzamide hydrochloride described at manufacturing example 5 and 60 mg (0.43 mmol, 4.0 eq.) potassium carbonate and 18 mg (0.12 mmol, 1.1 eq.) m-toluoyl chloride.

$^1$H NMR (400 MHz, DMSO-$d_6$) 1.08-1.18 (1H, m), 1.20-1.30 (1H, m), 1.50-1.60 (1H, m), 2.00-2.10 (1H, m), 2.32 (3H, s), 2.35-2.46 (8H, m), 2.58-2.68 (2H, m), 3.23-3.33 (2H, m), 3.52-3.62 (2H, m), 3.84 (2H, d), 4.10-4.20 (1H, m), 7.12-7.17 (2H, m), 7.22-7.32 (2H, m), 7.73 (1H, t), 7.91 (1H, d), 8.10-8.18 (2H, m), 8.21 (1H, s), 8.99 (1H, t)

Example 9

N-{[1-(2-(4-(4-methylbezoyl)piperazine-1-yl)ethyl)-pyrrolidine-(3R)-yl-carbamoyl]-methyl}-3-trifluoromethylbenzamide

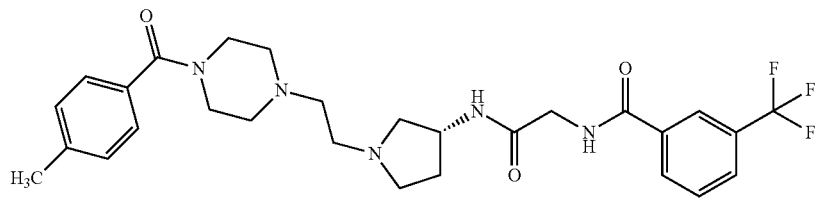 [SMILES: Cc1ccc(C(=O)N2CCN(CCN3CC[C@@H](NC(=O)CNC(=O)c4cccc(C(F)(F)F)c4)C3)CC2)cc1]

38 mg (65%) target compound as light-yellow solid was yielded on the same method as example 7 using 50 mg (0.11 mmol) N-{[1-(2-(piperazine-1-yl)ethyl)-pyrrolidine-(3R)-yl-carbamoyl]-methyl}-3-trifluoromethylbenzamide hydrochloride described at manufacturing example 5, 60 mg (0.43 mmol, 4.0 eq.) potassium carbonate and 18 mg (0.12 mmol, 1.1 eq.) p-toluoyl chloride.

$^1$H NMR (400 MHz, DMSO-$d_6$) 1.08-1.30 (2H, m), 1.50-1.60 (1H, m), 2.00-2.10 (1H, m), 2.32 (3H, s), 2.33-2.42 (8H, m), 2.58-2.68 (2H, m), 3.25-3.35 (2H, m), 3.50-3.60 (2H, m), 3.84 (2H, d), 4.10-4.20 (1H, m), 7.20-7.30 (4H, m), 7.73 (1H, t), 7.91 (1H, d), 8.11-8.18 (2H, m), 8.21 (1H, s), 8.99 (1H, t)

Example 10

N-{[1-(2-(4-(4-fluorobenzoyl)piperazine-1-yl)ethyl)-pyrrolidine-(3R)-yl-carbamoyl]-methyl}-3-trifluoromethylbenzamide

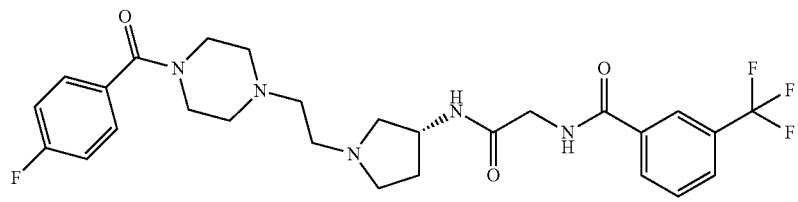 [SMILES: O=C(CNC(=O)c1cccc(C(F)(F)F)c1)N[C@@H]1CCN(CCN2CCN(C(=O)c3ccc(F)cc3)CC2)C1]

33 mg (55%) target compound as light-white solid was yielded on the same method as example 7 using 50 mg (0.11 mmol) N-{[1-(2-(piperazine-1-yl)ethyl)-pyrrolidine-(3R)-yl-carbamoyl]-methyl}-3-trifluoromethylbenzamide hydrochloride described at manufacturing example 5, 60 mg (0.43 mmol, 4.0 eq.) potassium carbonate and 19 mg (0.12 mmol, 1.1 eq.) 4-fluorobenzoyl chloride.

$^1$H NMR (400 MHz, DMSO-$d_6$) 1.50-1.60 (1H, m), 2.00-2.10 (1H, m), 2.30-2.50 (10H, m), 2.60-2.68 (2H, m), 3.25-3.35 (2H, m), 3.50-3.60 (2H, m), 3.84 (2H, d), 4.10-4.20 (1H, m), 7.22-7.30 (2H, m), 7.41-7.48 (2H, m), 7.73 (1H, t), 7.91 (1H, d), 8.12 (1H, d), 8.16 (1H, d), 8.21 (1H, s), 8.98 (1H, t)

Example 11

N-{[1-(2-(4-(4-cyanobenzoyl)piperazine-1-yl)ethyl)-pyrrolidine-(3R)-yl-carbamoyl]-methyl}-3-trifluoromethylbenzamide

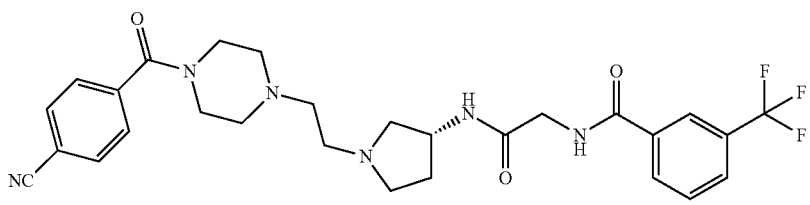 [SMILES: N#Cc1ccc(C(=O)N2CCN(CCN3CC[C@@H](NC(=O)CNC(=O)c4cccc(C(F)(F)F)c4)C3)CC2)cc1]

42 mg (70%) target compound as light-white solid was yielded on the same method as example 7 using 50 mg (0.11 mmol) N-{[1-(2-(piperazine-1-yl)ethyl)-pyrrolidine-(3R)-yl-carbamoyl]-methyl}-3-trifluoromethylbenzamide hydrochloride described at manufacturing example 5, 60 mg (0.43 mmol, 4.0 eq.) potassium carbonate and 20 mg (0.12 mmol, 1.1 eq.) 4-cyanobenzoyl chloride.

$^1$H NMR (400 MHz, DMSO-$d_6$) 1.52-1.62 (1H, m), 2.00-2.10 (1H, m), 2.30-2.55 (10H, m), 2.60-2.70 (2H, m), 3.19-3.25 (2H, m), 3.58-3.63 (2H, m), 3.84 (2H, d), 4.10-4.20 (1H, m), 7.55 (2H, d), 7.73 (1H, t), 7.88-7.94 (3H, m), 8.12-8.18 (2H, m), 8.21 (1H, s), 8.99 (1H, t)

Example 12

N-{[1-(2-(4-(4-ethylbenzoyl)piperazine-1-yl)ethyl)-pyrrolidine-(3R)-yl-carbamoyl]-methyl}-3-trifluoromethylbenzamide Example 13

N-{[1-(2-(4-(phenylsulfonyl)piperazine-1-yl)ethyl)-pyrrolidine-(3R)-yl-carbamoyl]-methyl}-3-trifluoromethylbenzamide

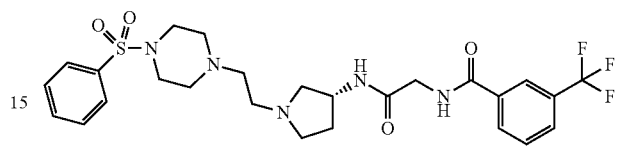

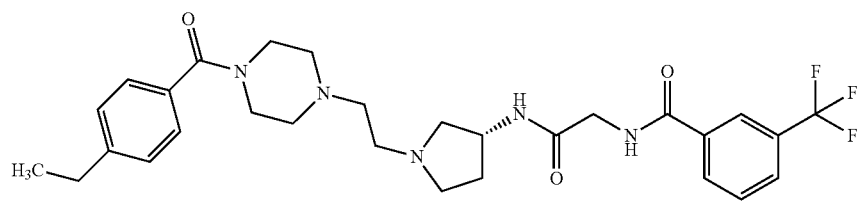 [SMILES: CCc1ccc(C(=O)N2CCN(CCN3CC[C@@H](NC(=O)CNC(=O)c4cccc(C(F)(F)F)c4)C3)CC2)cc1]

48 mg (79%) target compound as white solid was yielded on the same method as example 7 using 50 mg (0.11 mmol) N-{[1-(2-(piperazine-1-yl)ethyl)-pyrrolidine-(3R)-yl-carbamoyl]-methyl}-3-trifluoromethylbenzamide hydrochloride described at manufacturing example 5, 60 mg (0.43 mmol, 4.0 eq.) potassium carbonate and 20 mg (0.12 mmol, 1.1 eq.) 4-ethylbenzoyl chloride.

$^1$H NMR (400 MHz, DMSO-$d_6$) 1.08-1.28 (5H, m), 1.50-1.60 (1H, m), 2.00-2.10 (1H, m), 2.32-2.47 (10H, m), 2.57-2.68 (4H, m), 3.50-3.60 (2H, m), 3.84 (2H, d), 4.10-4.19 (1H, m), 7.23-7.32 (4H, m), 7.73 (1H, t), 7.84 (1H, d), 7.91 (1H, d), 8.16 (1H, d), 8.21 (1H, s), 8.99 (1H, t)

34 mg (55%) target compound as light-white solid was yielded on the same method as example 7 using 50 mg (0.11 mmol) N-{[1-(2-(piperazine-1-yl)ethyl)-pyrrolidine-(3R)-yl-carbamoyl]-methyl}-3-trifluoromethylbenzamide hydrochloride described at manufacturing example 5, 60 mg (0.43 mmol, 4.0 eq.) potassium carbonate and 21 mg (0.12 mmol, 1.1 eq.) benzensulfonyl chloride.

$^1$H NMR (400 MHz, DMSO-$d_6$) 1.08-1.30 (2H, m), 1.48-1.56 (1H, m), 1.96-2.06 (1H, m), 2.25-2.60 (10H, m), 2.80-2.90 (4H, m), 3.82 (2H, d), 4.08-4.15 (1H, m), 7.62-7.68 (2H, m), 7.70-7.76 (4H, m), 7.91 (1H, d), 8.05-8.13 (1H, m), 8.15 (1H, d), 8.20 (1H, s), 8.94-9.00 (1H, m)

Example 14

N-{[1-(2-(4-propionlypiperazine-1-yl)ethyl)-pyrrolidine-(3R)-yl-carbamoyl]-methyl}-3-trifluoromethylbenzamide

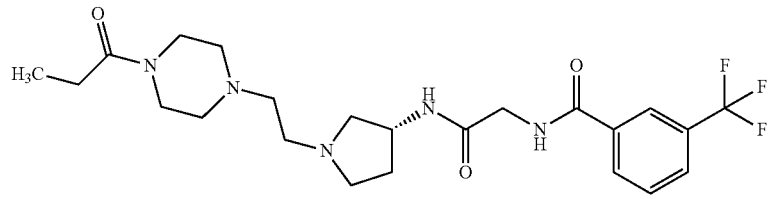

42 mg (81%) target compound as yellow solid was yielded on the same method as example 7 using 50 mg (0.11 mmol) N-{[1-(2-(piperazine-1-yl)ethyl)-pyrrolidine-(3R)-yl-carbamoyl]-methyl}-3-trifluoromethylbenzamide hydrochloride described at manufacturing example 5, 60 mg (0.43 mmol, 4.0 eq.) potassium carbonate and 11 mg (0.12 mmol, 1.1 eq.) propionyl chloride.

$^1$H NMR (400 MHz, DMSO-$d_6$) 0.95 (3H, t), 1.50-1.60 (1H, m), 2.00-2.10 (1H, m), 2.25-2.40 (10H, m), 2.48-2.58 (2H, m), 2.58-2.68 (2H, m), 3.32-3.42 (4H, m), 3.84 (2H, d), 4.10-4.20 (1H, m), 7.73 (1H, t), 7.91 (1H, d), 8.12 (1H, d), 8.16 (1H, d), 8.21 (1H, s), 8.99 (1H, t)

Example 15

N-{[1-(2-(4-benzylpiperazine-1-yl)ethyl)-pyrrolidine-(3R)-yl-carbamoyl]-methyl}-3-trifluoromethylbenzamide

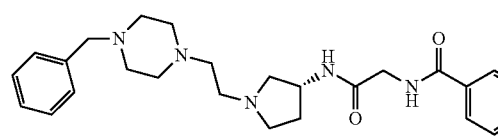

0.042 g (75%) target compound as yellow solid was yielded on the same method as example 7 using 50 mg (0.11 mmol) N-{[1-(2-(piperazine-1-yl)ethyl)-pyrrolidine-(3R)-yl-carbamoyl]-methyl}-3-trifluoromethylbenzamide hydrochloride described at manufacturing example 5, 60 mg (0.43 mmol, 4.0 eq.) potassium carbonate and 14 mg (0.11 mmol, 1.1 eq.) benzyl chloride.

$^1$H NMR (400 MHz, CDCl$_3$) 1.63-1.79 (1H, m), 2.26-2.39 (2H, m), 2.40-2.57 (10H, m), 2.61-2.77 (3H, m), 2.91 (1H, d), 3.08-3.14 (1H, m), 3.51 (2H, s), 4.08-4.17 (2H, m), 4.50-4.58 (1H, m), 7.23-7.35 (6H, m), 7.39 (1H, d), 7.58 (1H, t), 7.77 (1H, d), 8.03 (1H, d), 8.13 (1H, s)

Example 16

N-{[1-(1-(4-benzoylpiperazine-1-yl)propane-2-yl)-pyrrolidine-(3R)-yl-carbamoyl]-methyl}-3-trifluoromethylbenzamide 100 mg (0.32 mmol) N-(pyrrolidine-(3R)-yl-carbamoylmethyl)-3-trifluoromethylbenzamide described at manufacturing example 3 and 80 mg (0.32 mmol, 1.0 eq.) 1-(4-benzoylpiperazine-1-yl)propane-2-on described at manufacturing example 10 were dissolved into 10 ml dichloroethane. After 200 mg (0.95 mmol, 3.0 eq.) sodium triacetoxyborohydride was added and stirred 5 hours at room temperature, 50 ml sodium bicarbonate saturated aqueous solution was added and reaction mixture was extracted with 30 ml ethylacetate. After separating organic layer and drying with anhydrous magnesium sulfate, it was purified by chromatography using silicagel (mobile phase: dichloromethane/methanol=25:1) and 120 mg (70%) target compound as pale yellow solid was yielded.

$^1$H NMR (400 MHz, DMSO-$d_6$) 1.00-1.09 (3H, m), 1.48-1.60 (1H, m), 1.96-2.10 (1H, m), 2.12-2.23 (1H, m), 2.24-2.55 (10H, m), 2.65-2.81 (2H, m), 3.53-3.66 (2H, m), 3.87 (2H, d), 4.07-4.17 (1H, m), 7.34-7.38 (2H, m), 7.42-7.48 (3H, m), 7.74 (1H, t), 7.92 (1H, d), 8.03-8.12 (1H, m), 8.17 (1H, d), 8.22 (1H, s), 8.93-9.03 (1H, m)

MS (M+1)$^+$ 546.4

Example 17

N-{[1-(3-(4-benzoylpiperazine-1-yl)butane-2-yl)-pyrrolidine-(3R)-yl-carbamoyl]-methyl}-3-trifluoromethylbenzamide

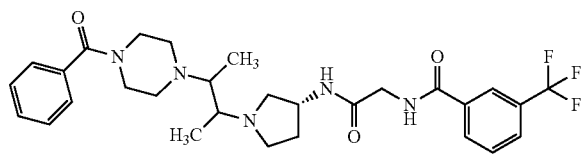 [SMILES: CC(C(C)N1CC[C@@H](NC(=O)CNC(=O)c2cccc(C(F)(F)F)c2)C1)N1CCN(C(=O)c2ccccc2)CC1]

50 mg (0.19 mmol) 3-(4-benzoylpiperazine-1-yl)butane-2-on described at manufacturing example 11 and 120 mg (0.38 mmol, 2.0 eq.) N-(pyrrolidine-(3R)-yl-carbamoylmethyl)-3-trifluoromethylbenzamide described at manufacturing example 3 were dissolved to 5 ml dichloroethane. After adding 200 mg (0.96 mmol, 5.0 eq.) sodium triacetoxyborohydride and stirring for 24 hours at room temperature, 25 ml sodium bicarbonate saturated aqueous solution was added and reaction mixture was extracted with 15 ml ethylacetate. After separating organic layer and drying with anhydrous magnesium sulfate, 40 mg (37%) target compound as pale yellow solid was yielded by purifying with chromatography (mobile phase: dichloromethane/methanol=25:1) using silicagel.

$^1$H NMR (400 MHz, DMSO-$d_6$) 0.92 (3H, d), 0.96 (3H, d), 1.48-1.62 (1H, m), 1.95-2.08 (1H, m), 2.31-2.48 (9H, m), 2.53-2.81 (3H, m), 3.48-3.67 (2H, m), 3.87 (2H, d), 4.08-4.17 (1H, m), 7.34-7.39 (2H, m), 7.43-7.48 (3H, m), 7.75 (1H, t), 7.93 (1H, d), 7.98 (1H, dd), 8.18 (1H, d), 8.22 (1H, s), 9.00 (1H, t)

MS (M+1)$^+$ 560.6

Example 18

N-{[1-(2-(4-benzoylpiperazine-1-yl)propane-1-yl)-pyrrolidine-(3R)-yl-carbamoyl]-methyl}-3-trifluoromethylbenzamide

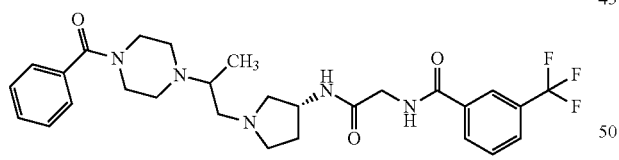

400 mg (1.07 mmol) N-{[1-(2-hydroxypropyl)-pyrrolidine-(3R)-yl-carbamoyl]-methyl}-3-trifluoromethylbenzamide and 0.18 ml (1.29 mmol, 1.2 eq.) triethylamine described at manufacturing example 6 were dissolved to 20 ml dichloromethane and cooled to 3° C. under argon gas. 135 mg (1.18 mmol, 1.1 eq.) methanesulfonyl chloride was slowly added to reaction solution and was stirred at same temperature for 30 min. 20 ml purified water was added and then organic layer was separated and concentrated with decompression. After 10 ml acetonitrile were added to obtained residues and dissolved them, 444 mg (3.21 mmol) potassium carbonate and 202 mg (1.06 mmol) 1-benzoylpiperazine were added. After stirring for 2 hours at room temperature, 15 ml saturated sodium chloride aqueous solution was added to reaction solution and was extracted twice with 15 ml ethylacetate. After organic layer was collected and dried with anhydrous magnesium sulfate, it was concentrated with decompression. 30 mg (51%) target compound as light-yellow solid was yielded by purifying obtained residues with chromatography using silicagel (mobile phase: dichloromethane/methanol=5:1 and 1:1).

$^1$H NMR (400 MHz, DMSO-$d_6$) 1.05 (3H, s), 1.55-1.65 (1H, m), 2.00-2.10 (1H, m), 2.15-2.25 (1H, m), 2.28-2.55 (9H, m), 2.70-2.85 (2H, m), 3.17 (1H, d), 3.54-3.65 (2H, m), 3.87 (2H, d), 4.10-4.20 (1H, m), 7.35-7.40 (2H, m), 7.40-7.47 (3H, m), 7.74 (1H, t), 7.92 (1H, d), 8.14 (1H, s), 8.18 (1H, d), 8.23 (1H, s), 9.01 (1H, t)

MS (M)$^+$ 545.6

Example 19

N-{[1-(1-(4-benzoylpiperazine-1-yl)butane-2-yl)-pyrrolidine-(3R)-yl-carbamoyl]-methyl}-3-trifluoromethylbenzamide

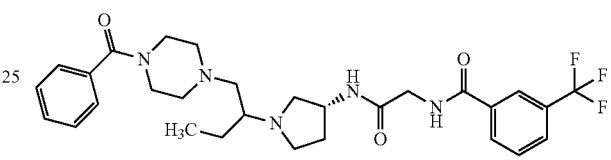

100 mg (0.38 mmol) 1-(4-benzoylpiperazine-1-yl)butane-2-on and 360 mg (1.15 mmol, 3.0 eq.) N-(pyrrolidine-(3R)-yl-carbamoylmethyl)-3-trifluoromethyl benzamide described at manufacturing example 3 were dissolved into 15 ml dichloroethane. After 490 mg (2.31 mmol, 6.0 eq.) sodium triacetoxyborohydride was added and was stirred for 3 hours at room temperature, 50 ml potassium bicarbonate saturated aqueous solution was added and reaction mixture was extracted with 50 ml ethylacetate. After organic layer was separated and dried with anhydrous magnesium sulfate, 150 mg (70%) target compound as pale yellow solid was yielded by purifying with chromatography using silicagel (mobile phase: dichloromethane/methanol=25:1).

$^1$H NMR (400 MHz, DMSO-$d_6$) 0.84 (3H, t), 1.42-1.61 (3H, m), 1.98-2.08 (1H, m), 2.22-2.29 (1H, m), 2.30-2.52 (10H, m), 2.63-2.83 (2H, m), 3.53-3.67 (2H, m), 3.87 (2H, d), 4.08-4.19 (1H, m), 7.34-7.40 (2H, m), 7.42-7.48 (3H, m), 7.74 (1H, t), 7.92 (1H, d), 8.02 (1H, d), 8.18 (1H, d), 8.22 (1H, s), 8.99 (1H, t)

MS (M+1)$^+$ 560.7

Example 20

N-{[1-(2-(4-benzoylpiperazine-1-yl) butyl)-pyrrolidine-(3R)-yl-carbamoyl]-methyl}-3-trifluoromethylbenzamide

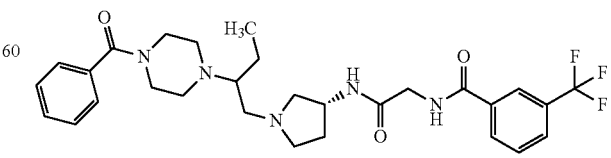

21 mg (35%) target compound as yellow solid was yielded on the same method as example 18 using 415 mg (1.07 mmol)

N-{[1-(2-hydroxybutyl)-pyrrolidine-(3R)-yl-carbamoyl]-methyl}-3-trifluoromethylbenzamide described at manufacturing example 7.

$^1$H NMR (400 MHz, DMSO-d$_6$) 0.84 (3H, t), 1.40-1.52 (2H, m), 1.98-2.08 (1H, m), 2.22-2.30 (1H, m), 2.30-2.58 (10H, m), 2.65-2.86 (3H, m), 3.50-3.66 (2H, m), 3.87 (2H, d), 4.10-4.18 (1H, m), 7.34-7.48 (5H, m), 7.74 (1H, t), 7.92 (1H, d), 8.05 (1H, d), 8.18 (1H, d), 8.23 (1H, s), 9.90 (1H, t)

MS (M+1)+560.8

Example 21

N-{[1-(2-(4-benzoylpiperazine-1-yl)-2-methylpropyl)-pyrrolidine-(3R)-yl-carbamoyl]-methyl}-3-trifluoromethylbenzamide

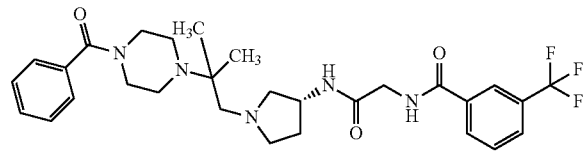 [SMILES: CC(C)(CN1CC[C@@H](NC(=O)CNC(=O)c2cccc(C(F)(F)F)c2)C1)N1CCN(C(=O)c2ccccc2)CC1]

27 mg (45%) target compound as light-yellow solid was yielded on the same method as example 18 using 415 mg (1.07 mmol) N-{[1-(2-hydroxy-2-methylpropyl)-pyrrolidine-(3R)-yl-carbamoyl]-methyl}-3-fluoromethylbenzamide described at manufacturing example 8.

$^1$H NMR (400 MHz, DMSO-d$_6$) 0.80-0.90 (1H, m), 0.92-1.00 (6H, m), 1.15-1.25 (1H, m), 1.51-1.60 (1H, m), 1.92-2.08 (1H, m), 2.35-2.62 (6H, m), 2.65-2.88 (2H, m), 3.20-3.32 (2H, m), 3.50-3.62 (2H, m), 3.85-3.90 (2H, m), 4.00-4.18 (1H, m), 7.35-7.40 (2H, m), 7.40-7.48 (3H, m), 7.74 (1H, t), 7.93 (1H, d), 8.02 (1H, d), 8.18 (1H, d), 8.23 (1H, s), 8.98-9.03 (1H, m)

Example 22

N-{[1-(1-(4-benzoylpiperazine-1-yl)-2-methylpropan-2-yl)-pyrrolidine-(3R)-yl-carbamoyl]-methyl}-3-trifluoromethylbenzamide

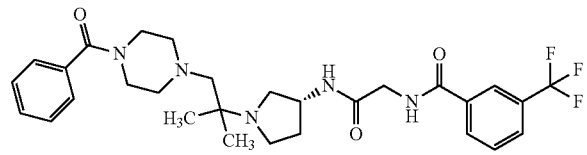 [SMILES: CC(C)(CN1CCN(C(=O)c2ccccc2)CC1)N1CC[C@@H](NC(=O)CNC(=O)c2cccc(C(F)(F)F)c2)C1]

60 mg (0.23 mmol)(4-(2-hydroxy-2-methylpropyl)piperazine-1-yl)phenylmethanone described at manufacturing example 9 and 28 mg (0.25 mmol, 1.1 eq.) triethylamine were dissolved into 5 ml dichloromethane and cooled to 3° C. under argon gas. 29 mg (0.25 mmol, 1.1 eq.) Methansulfonyl chloride was slowly added to reaction solution and then it was stirred for 1.5 hour at same temperature. 5 ml purified water was added and then organic layer was separated and it was concentrated with decompression. After 5 ml acetonitrile was added to obtained residues and dissolved them, 76 mg (0.55 mmol) potassium carbonate and 58 mg (0.18 mmol) N-(pyrrolidine-(3R)-yl-carbamoylmethyl)-3-fluoromethylbenzamide described at manufacturing example 3 was added. After stirring for 3 hours at room temperature, 10 ml saturated sodium chloride aqueous solution was added to reaction solution and it was extracted twice with 10 ml ethylacetate. Organic layer was collected and dried with anhydrous magnesium sulfate and then concentrated with decompression. 57 mg (45%) target compound as light-yellow solid was yielded by purifying obtained residues with chromatography using silicagel (mobile phase: dichloromethane/methanol=5:1 and 1:1).

$^1$H NMR (400 MHz, DMSO-d$_6$) 0.92-1.00 (6H, m), 1.50-1.60 (1H, m), 1.92-2.08 (1H, m), 2.30-2.60 (8H, m), 2.64-2.78 (1H, m), 2.80-2.88 (1H, m), 3.30-3.62 (4H, m), 3.83-3.90 (2H, m), 4.05-4.18 (1H, m), 7.35-7.40 (2H, m), 7.40-7.47 (3H, m), 7.74 (1H, t), 7.92 (1H, d), 8.04 (1H, d), 8.18 (1H, d), 8.23 (1H, s), 9.06-9.13 (1H, m)

Example 23

N-{[1-(3-(4-(3-chlorophenyl)piperazine-1-yl)butane-2-yl)-pyrrolidine-(3R)-yl-carbamoyl]-methyl}-3-trifluoromethylbenzamide

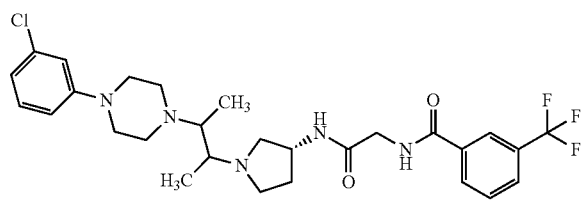 [SMILES: CC(C(C)N1CC[C@@H](NC(=O)CNC(=O)c2cccc(C(F)(F)F)c2)C1)N1CCN(c2cccc(Cl)c2)CC1]

100 mg (0.37 mmol)-3-(4-(3-chlorophenyl)piperazine-1-yl)butane-2-on and 240 mg (0.75 mmol, 2.0 eq.) N-(pyrrolidine-(3R)-yl-carbamoylmethyl)-3-trifluoromethylbenzamide described at manufacturing example 3 were dissolved into 10 ml dichloroethane. 480 mg (2.25 mmol, 6.0 eq.) sodium triacetoxyborohydride was added and stirred for 7 hours at room temperature, 30 ml potassium bicarbonate saturated aqueous solution was added and it was extracted with 20 ml ethylacetate. Organic layer was separated and dried with anhydrous magnesium sulfate, 140 mg (66%) target compound as white solid was yielded by purifying with chromatography using silicagel (mobile phase: dichloromethane/methanol=25:1).

$^1$H NMR (400 MHz, DMSO-d$_6$) 0.91-1.05 (6H, m), 1.48-1.64 (1H, m), 1.97-2.19 (1H, m), 2.32-2.41 (1H, m), 2.53-2.85 (9H, m), 3.05-3.20 (4H, m), 3.87 (2H, d), 4.07-4.20 (1H, m), 6.76 (1H, d), 6.87 (1H, d), 6.91 (1H, s), 7.19 (1H, t), 7.74 (1H, t), 7.93 (1H, d), 7.97-8.03 (1H, m), 8.18 (1H, d), 8.23 (1H, s), 9.02 (1H, s)

Example 24

N-{[1-(1-(4-phenylpiperazine-1-yl)propane-2-yl)-pyrrolidine-(3R)-yl-carbamoyl]-methyl}-3-trifluoromethylbenzamide

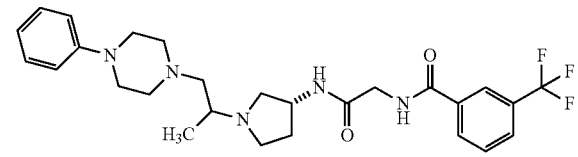

130 mg (55%) target compound as white solid was yielded on the same method as example 23 using 100 mg (0.46 mmol) 1-(4-phenylpiperazine-1-yl) propane-2-on and 290 mg (0.92 mmol, 2.0 eq.) N-(pyrrolidine-(3R)-yl-carbamoylmethyl)-3-trifluoromethylbenzamide described at manufacturing example 3, 580 mg (2.75 mmol, 6.0 eq.) sodium triacetoxyborohydride.

$^1$H HMR (400 MHz, DMSO-$d_6$) 1.06 (3H, t), 1.53-1.62 (1H, m), 2.00-2.09 (1H, m), 2.17-2.25 (1H, m), 2.41-2.62 (8H, m), 2.70-2.83 (2H, m), 3.07-3.15 (4H, m), 3.87 (2H, d), 4.10-4.20 (1H, m), 6.77 (1H, t), 6.91 (2H, d), 7.20 (2H, t), 7.74 (1H, t), 7.93 (1H, d), 8.09 (1H, d), 8.18 (1H, d), 8.23 (1H, s), 8.98 (1H, t)

Example 25

N-{[1-(1-(4-cyclohexylpiperazine-1-yl)propane-2-yl)-pyrrolidine(3R)-yl-carbamoyl]-methyl}-3-trifluoromethylbenzamide

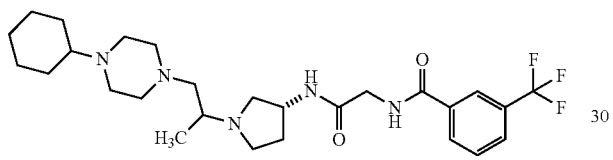

100 mg (43%) target compound as white solid was yielded on the same method as example 23 using 100 mg (0.45 mmol) 1-(4-cyclohexylpiperazine-1-yl) propane-2-on and 280 mg (0.89 mmol, 2.0 eq.) N-(pyrrolidine-(3R)-yl-carbamoylmethyl)-3-trifluoromethylbenzamide described at manufacturing example 3, 570 mg (2.67 mmol, 6.0 eq.) sodium triacetoxyborohydride.

$^1$H NMR (400 MHz, DMSO-$d_6$) 1.00 (3H, t), 1.03-1.21 (6H, m), 1.50-1.61 (2H, m), 1.68-1.79 (4H, m), 2.01-2.05 (1H, m), 2.06-2.12 (1H, m), 2.13-2.19 (1H, m), 2.30-2.41 (4H, m), 2.42-2.51 (7H, m), 2.65-2.82 (2H, m), 3.87 (2H, d), 4.08-4.17 (1H, m), 7.74 (1H, t), 7.93 (1H, d), 8.06 (1H, d), 8.18 (1H, d), 8.23 (1H, s), 8.97 (1H, t)

Example 26

N-{[1-(2-(4-(2-hydroxybutyl)piperazine-1-yl)ethyl)-pyrrolidine-(3R)-yl-carbamoyl]-methyl}-3-trifluoromethylbenzamide

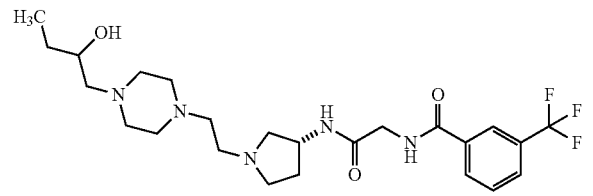

100 mg (0.19 mmol) N-{[1-(2-(piperazine-1-yl)ethyl)-pyrrolidine-(3R)-yl-carbamoyl]-methyl}-3-trifluoromethylbenzamide hydrochloride and 129 mg (0.93 mmol, 5.0 eq.) potassium carbonate described at manufacturing example 5 were suspended into 3 ml acetonitrile. 13 mg (0.19 mmol) 2-ethyloxirane was added, refluxed at 80° C. overnight, stirred and then cooled to room temperature. 15 ml purified water was added and then reaction mixture was extracted three times with 15 ml ethylacetate. Organic layer was collected, dried with anhydrous magnesium sulfate and concentrated with decompression. 73 mg (78%) target compound as white solid was yielded by purifying obtained residues with chromatography using silicagel. (mobile phase: dichloromethane/methanol=1:1)

MS (M+1)$^+$ 500.6

Example 27

N-{[1-(2-(4-(2-hydroxy-2-methylpropyl)piperazine-1-yl)ethyl)-pyrrolidine-(3R)-yl-carbamoyl]-methyl}-3-trifluoromethylbenzamide

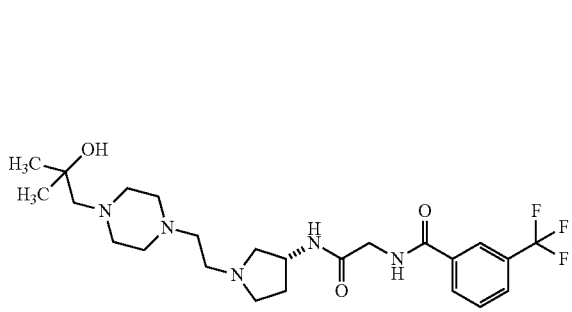

62 mg (67%) target compound as white solid was yielded on the same method as example 26 using 100 mg (0.19 mmol) N-{[1-(2-(piperazine-1-yl)ethyl)-pyrrolidine-(3R)-yl-carbamoyl]-methyl}-3-trifluoromethylbenzamide hydrochloride described at manufacturing example 5, 129 mg (0.93 mmol, 5.0 eq.) potassium carbonate and 13 mg (0.19 mmol) 2,2-dimethyloxirane.

MS (M+1)$^+$ 500.6

Example 28

N-{[1-(2-(4-(2-hydroxy-2-phenylethyl)piperazine-1-yl)ethyl)-pyrrolidine-(3R)-yl-carbamoyl]-methyl}-3-trifluoromethylbenzamide

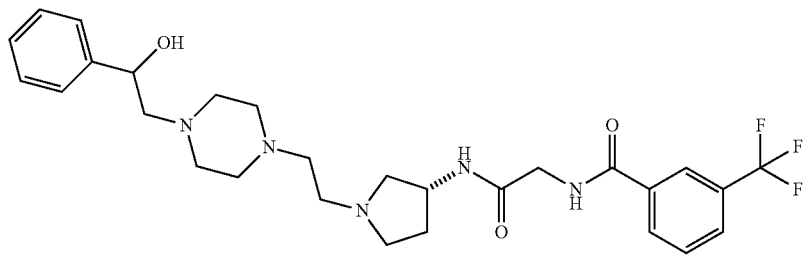

63 mg (62%) target compound as yellow solid was yielded on the same method as example 26 using 100 mg (0.19 mmol) N-{[1-(2-(piperazine-1-yl)ethyl)-pyrrolidine-(3R)-yl-carbamoyl]-methyl}-3-trifluoromethylbenzamide hydrochloride described at manufacturing example 5, 129 mg (0.93 mmol, 5.0 eq.) potassium carbonate and 22 mg (0.19 mmol) 2-phenyloxirane.

MS (M+1)+ 548.3

Example 29

N-{[1-(2-(4-(2-(4-chlorophenyl)-2-hydroxyethyl)piperazine-1-yl)ethyl)-pyrrolidine-(3R)-yl-carbamoyl]-methyl}-3-trifluoromethylbenzamide

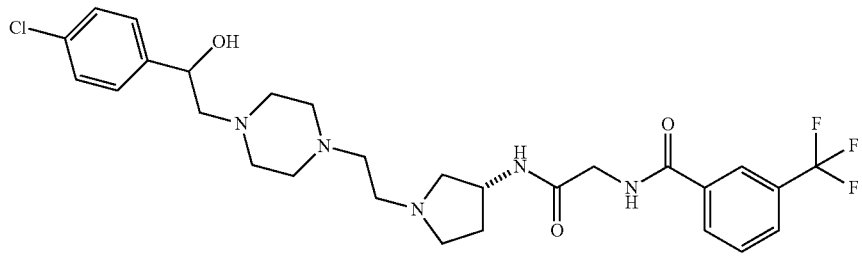

77 mg (71%) target compound as white solid was yielded on the same method as example 26 using 100 mg (0.19 mmol) N-{[1-(2-(piperazine-1-yl)ethyl)-pyrrolidine-(3R)-yl-carbamoyl]-methyl}-3-trifluoromethylbenzamide hydrochloride described at manufacturing example 5, 129 mg (0.93 mmol, 5.0 eq.) potassium carbonate and 23 mg (0.19 mmol) 2-(4-chlorophenyl) oxirane.

MS (M)+ 582.3

Example 30

N-{[1-(2-(4-benzoylpiperazine-1-yl)-2-oxoethyl)-pyrrolidine-(3R)-yl-carbamoyl]-methyl}-3-trifluoromethylbenzamide

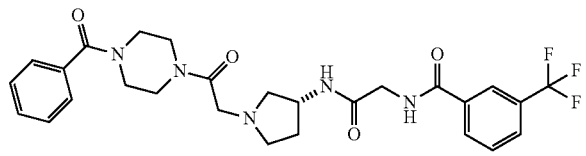

100 mg (0.21 mmol) N-{[1-(2-(piperazine-1-yl)-2-oxoethyl)-pyrrolidine-(3R)-yl-carbamoyl]-methyl}-3-trifluoromethylbenzamide hydrochloride and 120 mg (0.83 mmol, 4.0 eq.) potassium carbonate described at manufacturing example 14 were suspended into 10 ml acetonitrile at room temperature and then 30 mg (0.21 mmol, 1.0 eq.) benzoyl-chloride diluted into 1 ml acetonitrile was slowly added. It was heated with reflux, stirred for one hour and then concentrated with decompression. 10 ml purified water was added to obtained residues and then it was extracted twice with 10 ml ethylacetate. Organic layer was collected, dried with anhydrous magnesium sulfate, and concentrated with decompression. 70 mg (61%) target compound as white solid was yielded by purifying obtained residues with chromatography using silicagel (mobile phase: dichloromethane/methanol=25:1).

$^1$H NMR (400 MHz, DMSO-$d_6$) 1.53-1.68 (1H, m), 2.01-2.11 (1H, m), 2.37-2.48 (2H, m), 2.66 (1H, d), 2.73 (1H, t), 3.42-3.68 (10H, m), 3.84 (2H, d), 4.10-4.21 (1H, m), 7.38-7.41 (2H, m), 7.42-7.48 (3H, m), 7.72 (1H, t), 7.91 (1H, t), 8.12 (1H, d), 8.16 (1H, d), 8.21 (1H, s), 8.99 (1H, t)

MS (M+1)$^+$ 546.2

Example 31

N-{[1-(2-(4-(4-methylbenzoyl)piperazine-1-yl)-2-oxoethyl)-pyrrolidine-(3R)-yl-carbamoyl]-methyl}-3-trifluoromethylbenzamide

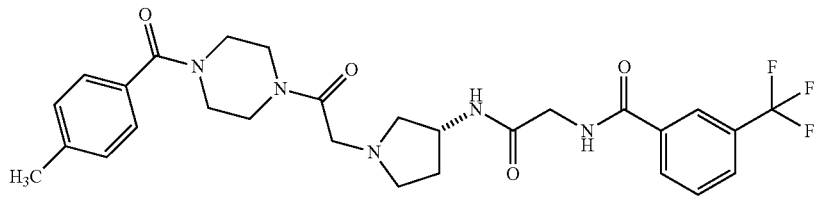

20 mg (34%) target compound as white solid was yielded on the same method as example 30 using 50 mg (0.10 mmol) N-{[1-(2-(piperazine-1-yl)-2-oxo-ethyl)-pyrrolidine-(3R)-yl-carbamoyl]-methyl}-3-trifluoromethylbenzamide hydrochloride described at manufacturing example 14, 60 mg (0.42 mmol, 4.0 eq.) potassium carbonate and 20 mg (0.10 mmol, 1.0 eq.) 4-methylbenzoyl chloride.

$^1$H NMR (400 MHz, DMSO-$d_6$) 1.18 (3H, t), 1.53-1.66 (1H, m), 2.01-2.13 (1H, m), 2.38-2.47 (2H, m), 2.58-2.78 (4H, m), 3.38-3.47 (4H, m), 3.48-3.62 (4H, m), 3.84 (2H, d), 4.09-4.21 (1H, m), 7.26 (2H, d), 7.32 (2H, d), 7.72 (1H, t), 7.90 (1H, d), 8.11 (1H, d), 8.13 (1H, d), 8.21 (1H, s), 8.99 (1H, t)

Example 32

N-{[1-(2-(4-(4-ethylbenzoyl)piperazine-1-yl)-2-oxoethyl)-pyrrolidine-(3R)-yl-carbamoyl]-methyl}-3-trifluoromethylbenzamide

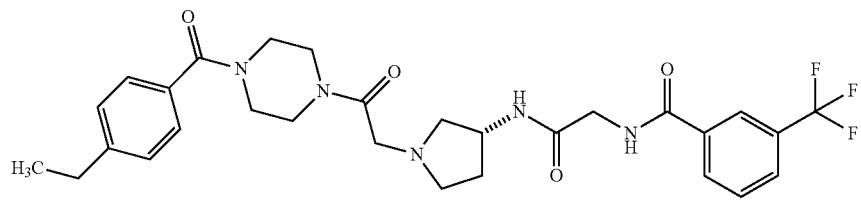

20 mg (33%) target compound as white solid was yielded on the same method as example 30 using 50 mg (0.10 mmol) N-{[1-(2-(piperazine-1-yl)-2-oxo-ethyl)-pyrrolidine-(3R)-yl-carbamoyl]-methyl}-3-trifluoromethylbenzamide hydrochloride described at manufacturing example 14, 60 mg (0.42 mmol, 4.0 eq.) potassium carbonate and 20 mg (0.10 mmol, 1.0 eq.) 4-ethylbenzoyl chloride.

$^1$H NMR (400 MHz, DMSO-$d_6$) 1.18 (3H, t), 1.53-1.65 (1H, m), 2.01-2.12 (1H, m), 2.37-2.48 (2H, m), 2.57-2.78 (4H, m), 3.25-3.35 (2H, m), 3.38-3.47 (4H, m), 3.48-3.65 (4H, m), 3.84 (2H, d), 4.11-4.22 (1H, m), 7.26 (2H, d), 7.32 (2H, d), 7.72 (1H, t), 7.90 (1H, d), 8.11 (1H, d), 8.16 (1H, d), 8.21 (1H, s), 8.99 (1H, t)

Example 33

N-{[1-(2-(4-(3-methylbenzoyl)piperazine-1-yl)-2-oxoethyl)-pyrrolidine-(3R)-yl-carbamoyl]-methyl}-3-trifluoromethylbenzamide

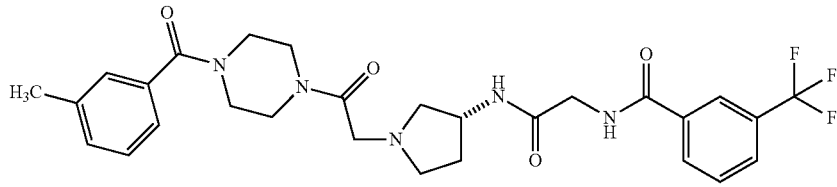

25 mg (43%) target compound as white solid was yielded on the same method as example 30 using 50 mg (0.10 mmol) N-{[1-(2-(piperazine-1-yl)-2-oxo-ethyl)-pyrrolidine-(3R)-yl-carbamoyl]-methyl}-3-trifluoromethylbenzamide hydrochloride described at manufacturing example 14, 60 mg (0.42 mmol, 4.0 eq.) potassium carbonate and 20 mg (0.10 mmol, 1.0 eq.) 3-methylbenzoyl chloride.

$^1$H NMR (400 MHz, DMSO-$d_6$) 1.62-1.75 (1H, m), 2.05-2.18 (1H, m), 2.34 (3H, s), 2.54-2.64 (2H, m), 2.68-2.97 (4H, m), 3.42-3.80 (8H, m), 3.87 (2H, d), 4.16-4.28 (1H, m), 7.20 (1H, d), 7.23 (1H, s), 7.27 (1H, d), 7.34 (1H, t), 7.74 (1H, t), 7.92 (1H, d), 8.18 (2H, d), 8.23 (1H, s), 9.04 (1H, t)

Example 34

N-{[1-(2-(4-(2-methylbenzoyl)piperazine-1-yl)-2-oxoethyl)-pyrrolidine-(3R)-yl-carbamoyl]-methyl}-3-trifluoromethylbenzamide

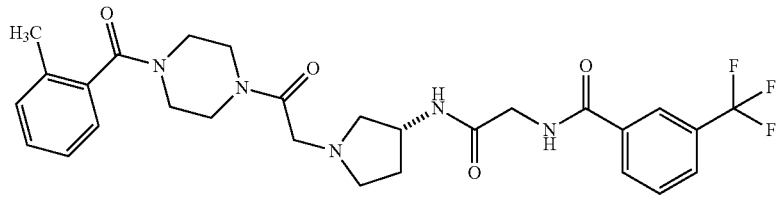

20 mg (34%) target compound as white solid was yielded on the same method as example 30 using 50 mg (0.10 mmol) N-{[1-(2-(piperazine-1-yl)-2-oxo-ethyl)-pyrrolidine-(3R)-yl-carbamoyl]-methyl}-3-trifluoromethylbenzamide hydrochloride described at manufacturing example 14, 60 mg (0.42 mmol, 4.0 eq.) potassium carbonate and 20 mg (0.10 mmol, 1.0 eq.) 2-methylbenzoyl chloride.

$^1$H NMR (400 MHz, DMSO-$d_6$) 1.62-1.82 (1H, m), 2.05-2.20 (1H, m), 2.22 (3H, s), 2.70-3.00 (6H, m), 3.17-3.22 (3H, m), 3.52-3.78 (5H, m), 3.87-3.93 (2H, m), 4.16-4.32 (1H, m), 7.20-7.38 (4H, m), 7.74 (1H, t), 7.93 (1H, t), 8.18 (1H, d), 8.23 (1H, s), 8.24-8.32 (1H, m), 9.02-9.09 (1H, m)

Example 35

N-{[1-(2-(4-phenylpiperazine-1-yl)-2-oxoethyl)-pyrrolidine-(3R)-yl-carbamoyl]-methyl}-3-trifluoromethylbenzamide

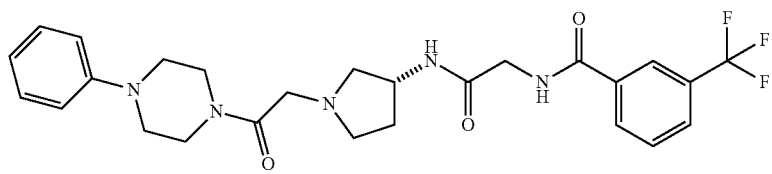

40 mg (49%) target compound as white solid was yielded on the same method as example 30 using 50 mg (0.16 mmol) N-(pyrrolidine-(3R)-yl-carbamoylmethyl)-3-trifluoromethylbenzamide described at manufacturing example 3, 90 mg (0.63 mmol, 4.0 eq.) potassium carbonate and 40 mg (0.16 mmol, 1.0 eq.) 2-chloro-1-(4-phenylpiperazine-1-yl)ethanone.

$^1$H NMR (400 MHz, DMSO-$d_6$) 1.57-1.68 (1H, m), 2.01-2.11 (1H, m), 2.37-2.48 (2H, m), 2.62-2.71 (1H, m), 2.78 (1H, t), 3.01-3.16 (4H, m), 3.27-3.32 (2H, m), 3.46-3.56 (2H, m), 3.58-3.67 (2H, m), 3.85 (2H, d), 4.11-4.22 (1H, m), 6.79 (1H, t), 6.93 (2H, d), 7.21 (2H, t), 7.72 (1H, t), 7.91 (1H, d), 8.16-8.18 (2H, m), 8.21 (1H, s), 8.98-9.03 (1H, m)

Example 36

N-{[1-(2-(4-benzoxycarbonyl)piperazine-1-yl)-2-oxoethyl)-pyrrolidine-(3R)-yl-carbamoyl]-methyl}-3-trifluoromethylbenzamide

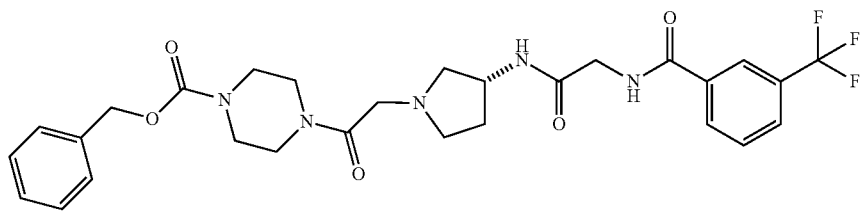

40 mg (44%) target compound as white solid was yielded on the same method as example 30 using 50 mg (0.16 mmol) N-(pyrrolidine-(3R)-yl-carbamoylmethyl)-3-trifluoromethylbenzamide described at manufacturing example 3, 90 mg (0.63 mmol, 4.0 eq.) potassium carbonate and 30 mg (0.16 mmol, 1.0 eq.) benzyl 4-(2-chloroacetyl)piperazine-1-carboxylate described at example 3.

$^1$H NMR (400 MHz, DMSO-$d_6$) 1.54-1.65 (1H, m), 2.01-2.10 (1H, m), 2.38-2.43 (1H, m), 2.44-2.47 (1H, m), 2.62-2.70 (1H, m), 2.73 (1H, t), 3.26-3.34 (4H, m), 3.38-3.45 (4H, m), 3.46-3.53 (2H, m), 3.85 (2H, d), 4.12-4.18 (1H, m), 5.08 (2H, s), 7.28-7.37 (5H, m), 7.72 (1H, t), 7.90 (1H, d), 8.13 (1H, d), 8.16 (1H, d), 8.22 (1H, s), 9.01 (1H, t)

Example 37

N-{[1-(2-(4-benzoyl-2,5-dimethylpiperazine-1-yl)ethyl)-pyrrolidine-(3R)-yl-carbamoyl]-methyl}-3-trifluoromethylbenzamide

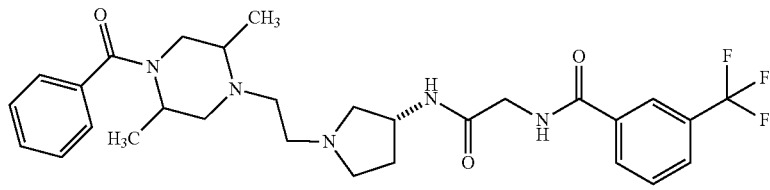

200 mg (0.56 mmol) N-{[1-(2-hydroxyethyl)-pyrrolidine-(3R)-yl-carbamoyl]-methyl}-3-trifluoromethylbenzamide and 68 mg (0.69 mmol, 1.2 eq.) triethylamine were dissolved into 10 ml dichloromethane and cooled to 3° C. under argon gas. 70 mg (0.61 mmol, 1.1 eq.) methanesulfonyl chloride was slowly added to reaction solution and then it was stirred for one hour at the same temperature. 10 ml purified water was added and then organic layer was separated, and concentrated with decompression. 10 ml acetonitrile was added to dissolve obtained residues and then 247 mg (1.78 mmol) potassium carbonate and 114 mg (0.45 mmol) 1-benzoyl-2,5-dimethylpiperazine hydrochloride were added. After stirring for 4 hours at room temperature, 20 ml saturated sodium chloride aqueous solution was added to reaction solution and was extracted twice with 20 ml ethylacetate. Organic layer was collected, dried with anhydrous magnesium sulfate, and concentrated with decompression. 159 mg (51%) target compound as light-yellow solid was yielded by purifying obtained residues with chromatography using silicagel (mobile phase: dichloromethane/methanol=5:1 and 1:1).

MS (M+1)$^+$ 560.4

Preferred embodiments of the present invention have been described above, but these embodiments are only for illustrative purposes and are not intended to limit the scope of the invention by any means. A person having ordinary skill in the art would understand that various deletions, substitutions and modifications can be carried out without departing from the spirit of the present invention. Therefore, the scope of the present invention should not be construed to be limited to these embodiments, but should be defined by the appended claims and their equivalents.

The invention claimed is:
1. Compound having the following formula I

[Formula 1]

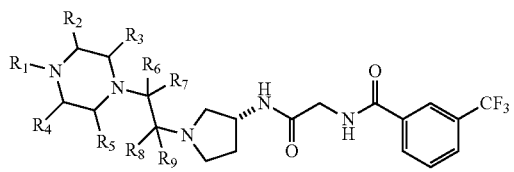

[Formula 2]

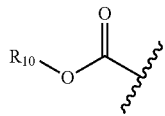

-continued

[Formula 3]

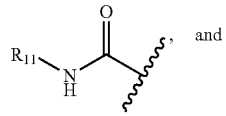, and

[Formula 4]

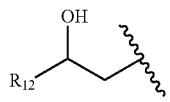

wherein:
   $R_1$ can be independently selected from the group consisting of hydrogen atom, $C_1$-$C_3$ alkyl, phenyl, benzyl, benzoyl, benzensulfonyl, $C_1$-$C_3$ alkylcarbonyl, $C_3$-$C_7$ cycloalkyl, the formula II, III and IV;
   $R_{10}$, $R_{11}$ and $R_{12}$ can be independently selected from the group consisting of hydrogen atom, $C_1$-$C_3$ alkyl, phenyl, and benzyl;
all benzene groups included as part of $R_1$ can have a plurality of substituents independently selected from the group consisting of $C_1$-$C_3$ alkyl, $C_1$-$C_2$ haloalkyl, halogen atom and cyano;
   $R_2$, $R_3$, $R_4$, $R_5$, $R_6$, $R_7$, $R_8$ and $R_9$ can be independently selected from hydrogen atom and $C_1$-$C_3$ alkyl;
   $R_6$ and $R_7$, $R_8$ and $R_9$ can be independently selected as carbonyl group;
   wherein said halogen is selected from the group consisting of fluorine, chlorine and bromine atom.

2. Compound according to claim 1, wherein the compound is selected from the group consisting of
   N-{[1-(2-(1-(phenylaminocarbonyl)-piperazine-4-yl)ethyl)-pyrrolidine-(3R)-yl-carbamoyl]-methyl}-3-trifluoromethylbenzamide,
   N-{[1-(2-(1-(p-tolylaminocarbonyl)-piperazine-4-yl)-ethyl)-pyrrolidine-(3R)-yl-carbamoyl]-methyl}-3-trifluoromethylbenzamide,
   N-{[1-(2-(1-(4-chlorophenylaminocarbonyl)-piperazine-4-yl)-ethyl)-pyrrolidine-(3R)-yl-carbamoyl]-methyl}-3-trifluoromethylbenzamide,
   N-{[1-(2-(1-(methoxycarbonyl)-piperazine-4-yl)ethyl)-pyrrolidine-(3R)-yl-carbamoyl]-methyl}-3-trifluoromethylbenzamide,
   N-{[1-(2-(1-(ethoxycarbonyl)-piperazine-4-yl)ethyl)-pyrrolidine-(3R)-yl-carbamoyl]-methyl}-3-trifluoromethylbenzamide,
   N-{[1-(2-(4-benzoylpiperazine-1-yl)ethyl)-pyrrolidine-(3R)-yl-carbamoyl]-methyl}-3-trifluoromethylbenzamide, N-{[1-(2-(4-(2-methylbenzoyl)piperazine-1-yl)ethyl)-pyrrolidine-(3R)-yl-carbamoyl]-methyl}-3-trifluoromethylbenzamide, N-{[1-(2-(4-(3-methylbenzoyl)piperazine-1-yl)ethyl)-pyrrolidine-(3R)-yl-carbamoyl]-methyl}-3-trifluoromethylbenzamide, N-{[1-(2-(4-(4-methylbenzoyl)piperazine-1-yl)ethyl)-pyrrolidine-(3R)-yl-carbamoyl]-methyl}-3-trifluoromethylbenzamide, N-{[1-(2-(4-(4-fluorobenzoyl)piperazine-1-yl)ethyl)-pyrrolidine-(3R)-yl-carbamoyl]-methyl}-3-trifluoromethylbenzamide, N-{[1-(2-(4-(4-cyanobenzoyl)piperazine-1-yl)ethyl)-pyrrolidine-(3R)-yl-carbamoyl]-methyl}-3-trifluoromethylbenzamide, N-{[1-(2-(4-(4-ethylbenzoyl)piperazine-1-yl)ethyl)-pyrrolidine-(3R)-yl-carbamoyl]-methyl}-3-trifluoromethylbenzamide, N-{[1-(2-(4-(phenylsulfonyl)piperazine-1-yl)ethyl)-pyrrolidine-(3R)-yl-carbamoyl]-methyl}-3-trifluoromethylbenzamide, N-{[1-(2-(4-propionylpiperazine-1-yl)ethyl)-pyrrolidine-(3R)-yl-carbamoyl]-methyl}-3-trifluoromethylbenzamide, N-{[1-(2-(4-benzylpiperazine-1-yl)ethyl)-pyrrolidine-(3R)-yl-carbamoyl]-methyl}-3-trifluoromethylbenzamide, N-{[1-(1-(4-benzoylpiperazine-1-yl)propane-2-yl)-pyrrolidine-(3R)-yl-carbamoyl]-methyl}-3-trifluoromethylbenzamide, N-{[1-(3-(4-benzoylpiperazine-1-yl)butane-2-yl)-pyrrolidine-(3R)-yl-carbamoyl]-methyl}-3-trifluoromethylbenzamide, N-{[1-(2-(4-benzoylpiperazine-1-yl)propane-1-yl)-pyrrolidine-(3R)-yl-carbamoyl]-methyl}-3-trifluoromethylbenzamide, N-{[1-(1-(4-benzoylpiperazine-1-yl)butane-2-yl)-pyrrolidine-(3R)-yl-carbamoyl]-methyl}-3-trifluoromethylbenzamide, N-{[1-(2-(4-benzoylpiperazine-1-yl)butyl)-pyrrolidine-(3R)-yl-carbamoyl]-methyl}-3-trifluoromethylbenzamide, N-{[1-(2-(4-benzoylpiperazine-1-yl)-2-methylpropyl)-pyrrolidine-(3R)-yl-carbamoyl]-methyl}-3-trifluoromethylbenzamide, N-{[1-(1-(4-benzoylpiperazine-1-yl)-2-methylpropan-2-yl)-pyrrolidine-(3R)-yl-carbamoyl]-methyl}-3-trifluoromethylbenzamide, N-{[1-(3-(4-(3-chlorophenyl)piperazine-1-yl)butane-2-yl)-pyrrolidine-(3R)-yl-carbamoyl]-methyl}-3-trifluoromethylbenzamide, N-{[1-(1-(4-phenylpiperazine-1-yl)propan-2-yl)-pyrrolidine-(3R)-yl-carbamoyl]-methyl}-3-trifluoromethylbenzamide, N-{[1-(1-(4-cyclohexylpiperazine-1-yl)propan-2-yl)-pyrrolidine(3R)-yl-carbamoyl]-methyl}-3-trifluoromethylbenzamide, N-{[1-(2-(4-(2-hydroxybutyl)piperazine-1-yl)ethyl)-pyrrolidine-(3R)-yl-carbamoyl]-methyl}-3-trifluoromethylbenzamide, N-{[1-(2-(4-(2-hydroxy-2-methylpropyl)piperazine-1-yl)ethyl)-pyrrolidine-(3R)-yl-carbamoyl]-methyl}-3-trifluoromethylbenzamide, N-{[1-(2-(4-(2-hydroxy-2-phenylethyl)piperazine-1-yl)ethyl)-pyrrolidine-(3R)-yl-carbamoyl]-methyl}-3-trifluoromethylbenzamide, N-{[1-(2-(4-(2-(4-chlorophenyl)-2-hydroxyethyl)piperazine-1-yl)ethyl)-pyrrolidine-(3R)-yl-carbamoyl]-methyl}-3-trifluoromethylbenzamide, N-{[1-(2-(4-benzoylpiperazine-1-yl)-2-oxoethyl)-pyrrolidine-(3R)-yl-carbamoyl]-methyl}-3-trifluoromethylbenzamide, N-{[1-(2-(4-(4-methylbenzoyl)piperazine-1-yl)-2-oxoethyl)-pyrrolidine-(3R)-yl-carbamoyl]-methyl}-3-trifluoromethylbenzamide, N-{[1-(2-(4-(4-ethylbenzoyl)piperazine-1-yl)-2-oxoethyl)-pyrrolidine-(3R)-yl-carbamoyl]-methyl}-3-trifluoromethylbenzamide, N-{[1-(2-(4-(3-methylbenzoyl)piperazine-1-yl)-2-oxoethyl)-pyrrolidine-(3R)-yl-carbamoyl]-methyl}-3-trifluoromethylbenzamide, N-{[1-(2-(4-(2-methylbenzoyl)piperazine-1-yl)-2-oxoethyl)-pyrrolidine-(3R)-yl-carbamoyl]-methyl}-3-trifluoromethylbenzamide, N-{[1-(2-(4-phenylpiperazine-1-yl)-2-oxoethyl)-pyrrolidine-(3R)-yl-carbamoyl]-methyl}-3-trifluoromethylbenzamide, N-{[1-(2-(4-(benzoxycarbonyl)piperazine-1-yl)-2-oxoethyl)-pyrrolidine-(3R)-yl-carbamoyl]-methyl}-3-trifluoromethylbenzamide, and N-{[1-(2-(4-benzoyl-2,5-dimethylpiperazine-1-yl)ethyl)-pyrrolidine-(3R)-yl-carbamoyl]-methyl}-3-trifluoromethylbenzamide.

3. Pharmaceutically acceptable salts and enantiomers, of the compound according to claim 1.

4. Pharmaceutical compositions which contain as an active ingredient, the compound according to claim 1 or a pharmaceutically acceptable salt thereof.

5. Pharmaceutical compositions according to claim 4, for inhibiting chemokine receptor (CCR2) activity in cells expressing CCR2 receptor protein.

6. Method of inhibiting chemokine receptor (CCR2) activity comprising, treating cells expressing CCR2 receptor protein with the compound according to claim 1 or a pharmaceutically acceptable salt thereof.

* * * * *